US011891609B2

(12) United States Patent
Tian et al.

(10) Patent No.: US 11,891,609 B2
(45) Date of Patent: *Feb. 6, 2024

(54) METHODS FOR INCREASING OBSERVED EDITING IN BACTERIA

(71) Applicant: Inscripta, Inc., Boulder, CO (US)

(72) Inventors: Tian Tian, Boulder, CO (US); Eileen Spindler, Boulder, CO (US); Charles Johnson, Boulder, CO (US); Clint Davis, Boulder, CO (US)

(73) Assignee: Inscripta, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/680,289

(22) Filed: Feb. 25, 2022

(65) Prior Publication Data

US 2022/0177899 A1   Jun. 9, 2022

Related U.S. Application Data

(63) Continuation of application No. 17/536,067, filed on Nov. 28, 2021, now Pat. No. 11,319,542, which is a continuation of application No. 16/952,024, filed on Nov. 18, 2020, now Pat. No. 11,203,762.

(60) Provisional application No. 62/937,289, filed on Nov. 19, 2019.

(51) Int. Cl.
*C12N 15/74* (2006.01)
*C12N 15/113* (2010.01)
*C12N 1/20* (2006.01)
*C12N 9/22* (2006.01)

(52) U.S. Cl.
CPC ............ *C12N 15/74* (2013.01); *C12N 1/20* (2013.01); *C12N 9/22* (2013.01); *C12N 15/113* (2013.01); *C12N 2310/20* (2017.05)

(58) Field of Classification Search
CPC . C12N 15/74; C12N 1/20; C12N 9/22; C12N 15/113; C12N 2310/20
See application file for complete search history.

(56) References Cited

U.S. PATENT DOCUMENTS

| 6,391,582 | B2 | 5/2002 | Ying et al. |
| 6,837,995 | B1 | 1/2005 | Vassarotti et al. |
| 7,166,443 | B2 | 1/2007 | Walker et al. |
| 8,332,160 | B1 | 12/2012 | Platt et al. |
| 8,697,359 | B1 | 4/2014 | Zhang et al. |
| 8,926,977 | B2 | 1/2015 | Miller et al. |
| 9,260,505 | B2 | 2/2016 | Weir et al. |
| 9,361,427 | B2 | 6/2016 | Hillson |
| 9,499,855 | B2 | 11/2016 | Hyde et al. |
| 9,776,138 | B2 | 10/2017 | Innings et al. |
| 9,790,490 | B2 | 10/2017 | Zhang et al. |
| 9,896,696 | B2 | 2/2018 | Begemann et al. |
| 9,982,278 | B2 | 5/2018 | Gill et al. |
| 9,982,279 | B1 | 5/2018 | Gill et al. |
| 9,988,624 | B2 | 6/2018 | Serber et al. |
| 10,011,849 | B1 | 7/2018 | Gill et al. |
| 10,017,760 | B2 | 7/2018 | Gill et al. |
| 10,227,576 | B1 | 3/2019 | Cameron et al. |
| 10,240,167 | B2 | 3/2019 | Gill et al. |
| 10,253,316 | B2 | 4/2019 | Masquelier et al. |
| 10,266,849 | B2 | 4/2019 | Gill et al. |
| 10,266,851 | B2 | 4/2019 | Chen |
| 10,323,242 | B1 | 6/2019 | Masquelier et al. |
| 10,323,258 | B2 | 6/2019 | Bernate et al. |
| 10,329,559 | B1 | 6/2019 | Masquelier et al. |
| 10,351,877 | B2 | 7/2019 | Gill et al. |
| 10,364,442 | B2 | 7/2019 | Gill et al. |
| 10,376,889 | B1 | 8/2019 | Masquelier et al. |
| 10,415,258 | B2 | 9/2019 | Gautreau et al. |
| 10,421,959 | B1 | 9/2019 | Masquelier et al. |
| 10,435,662 | B1 | 10/2019 | Masquelier et al. |
| 10,435,713 | B2 | 10/2019 | Bernate et al. |
| 10,435,715 | B2 | 10/2019 | Gill et al. |
| 10,443,031 | B1 | 10/2019 | Masquelier et al. |
| 10,443,074 | B2 | 10/2019 | Bernate et al. |
| 10,465,207 | B2 | 11/2019 | Garst et al. |
| 10,532,324 | B1 | 1/2020 | Masquelier et al. |

(Continued)

FOREIGN PATENT DOCUMENTS

| EP | 2395087 | 12/2011 |
| EP | 3199632 | 8/2017 |

(Continued)

OTHER PUBLICATIONS

Mieschendahl M et al. F'-Coded, Temperature-Sensitive lambda cI857 Repressor Gene for Easy Construction and Regulation of lambda Promoter-Dependent Expression Systems. 1985. Journal of Bacteriology. vol. 164, No. 3. p. 1366-1369. (Year: 1985).*
Stanton BC et al. Genomic mining of prokaryotic repressors for orthogonal logic gates. 2014. Nature Chemical Biology. vol. 10. p. 99-105. (Year: 2014).*
Bao, et al., "Genome-scale engineering of *Saccharomyces cerevisiae* with single-nucleotide precision", Nature Biotechnology, doi:10. 1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).

(Continued)

*Primary Examiner* — Paul J Holland
(74) *Attorney, Agent, or Firm* — Arnold & Porter Kaye Scholer LLP

(57) ABSTRACT

The present disclosure relates to methods for increasing observed editing rates in the surviving bacteria cells. The compositions and methods presented herein in combination lead to a phenomenon of "edit or die." Although less cells survive plating and editing, a large percentage of cells that do survive are multiple editors. In one experiment it was found that if a cell survives transformation, plating, and editing, 75% of the surviving cells are multiple editors; that is, 75% of the surviving cells were simultaneously edited with edits at two or more different locations within the bacterial genome.

20 Claims, 19 Drawing Sheets

(56) References Cited

U.S. PATENT DOCUMENTS

| | | |
|---|---|---|
| 10,533,152 B1 | 1/2020 | Belgrader et al. |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0123330 A1 | 5/2014 | Carlson et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0018427 A1 | 1/2016 | Streibl et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0298425 A1 | 10/2017 | Shapiro et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2018/0327761 A1 | 11/2018 | Duchateau et al. |
| 2018/0371498 A1 | 12/2018 | Gill et al. |
| 2019/0017072 A1 | 1/2019 | Ditommaso et al. |
| 2019/0062787 A1 | 2/2019 | Bernate et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0194693 A1 | 6/2019 | Gill et al. |
| 2019/0225928 A1 | 7/2019 | Masquelier et al. |
| 2019/0270987 A1 | 9/2019 | Masquelier et al. |
| 2019/0316120 A1 | 10/2019 | Masquelier et al. |
| 2019/0317537 A1 | 10/2019 | Cui et al. |
| 2019/0382707 A1 | 12/2019 | Masquelier et al. |
| 2020/0056139 A1 | 2/2020 | Garst et al. |
| 2020/0056143 A1 | 2/2020 | Garst et al. |
| 2020/0071660 A1 | 3/2020 | Spindler et al. |
| 2020/0080045 A1 | 3/2020 | Bernate et al. |
| 2020/0095533 A1 | 3/2020 | Garst et al. |
| 2020/0109398 A1 | 4/2020 | Rubens et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO 2017/223330 | 12/2017 |
| WO | WO 2018/015544 A1 | 1/2018 |
| WO | WO 2018/031950 | 2/2018 |
| WO | WO 2018/071672 | 4/2018 |
| WO | WO 2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |
| WO | WO2020/191102 | 9/2020 |
| WO | WO2020/191153 | 9/2020 |
| WO | WO2020/217057 | 10/2020 |
| WO | WO2021/207541 | 10/2021 |

OTHER PUBLICATIONS

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpf1 enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962.

(56) References Cited

OTHER PUBLICATIONS

Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.

(56) References Cited

OTHER PUBLICATIONS

Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR quides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.
Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechnology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS ONE, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A_1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Anzalone, et al., "Programmable large DNA deletion, replacement, integration, and inversion with twin prime editing and site-specific recombinases", bioRxiv, Nov. 2, 2021, doi:10.1101/2021.11.01.466790, p. 1-51.
Horwitz, et al., "Efficient Multiplexed Integration of Synergistic Alleles and Metabolic Pathways in Yeasts via CRISPR-Cas", Cell Systems 1, Jul. 29, 2015, doi:10.1016/j.cels.2015.02.001, p. 88-96.
Jillette, et al., "Split Selectable Markers", Nature Communications, Oct. 31, 2019, doi:10.1038/s41467-019-12891-2, p. 1-8.
Pavankumar, "Inteins: Localized Distribution, Gene Regulation, and Protein Engineering for Biological Applications", Microorganisms, Feb. 28, 2018, doi:10.3390/microorganisms6010019, p. 1-15.
Choi, et al., "Precise genomic deletions using paired prime editing", bioRxiv, Jan. 2, 2021, doi:10.1101/2020.12.30.424891, p. 1-32.
Lin, et al., "High-efficiency prime editing with optimized, paired pegRNAs in plants", Nature Biotechnology, Mar. 25, 2021, doi:10.1038/s41587-021-00868-w, p. 1-12.
Bolukbasi, et al., "Orthogonal Cas9-Cas9 chimeras provide a versatile platform for genome editing", Nature Communications, Nov. 19, 2018, doi:10.1038/s41467-018-07310-x, p. 1-12.
Kweon, et al., "Fusion guide RNAs for orthogonal gene manipulation with Cas9 and Cpf1", Nature Communications, Nov. 23, 2017, doi:10.1038/s41467-017-01650-w, p. 1-6.
International Search Report and Written Opinion for International Application No. PCT/US21/48578, dated Feb. 15, 2022, p. 1-12.
International Search Report and Written Opinion for International Application No. PCT/US21/61156, dated Mar. 3, 2022, p. 1-13.
U.S. Appl. No. 17/536,067, filed Nov. 28, 2021, which issued as U.S. Pat. No. 11,319,542 on May 3, 2022.
U.S. Appl. No. 16/952,024, filed Nov. 18, 2020, which issued as U.S. Pat. No. 11,203,762 on Dec. 21, 2021.
Choudhry, "High-Throughput Method for Automated Colony and Cell Counting by Digital Image Analysis Based on Edge Detection," *PLos One*, vol. 11, No. 2, e0148469, pp. 1-23 (Feb. 2016) (San Francisco, CA).
International Search Report dated Feb. 26, 2021, in International Patent Application No. PCT/US2020/061135, 2 pages.

(56) References Cited

OTHER PUBLICATIONS

Levin-Reisman, et al., "Automated imaging with ScanLag reveals previously undetectable bacterial growth phenotypes," *Nature Methods*, vol. 7, No. 9, pp. 737-739 (Sep. 2010) (London, England).
Mieschendahl et al., "F'-Coded, Temperature-Sensitive Lambda cI857 Repressor Gene for Easy Construction and Regulation of Lambda promoter-depedent expression systems," *Journal of Bacteriology*, vol. 164, No. 3, pp. 1366-1369 (Jun. 1985) (Washington, DC).
Stanton et al., "Genomic mining of prokaryotic repressors for orthogonal logic gates", *Nature Chemical Biology*, vol. 10, No. 2, pp. 99-105 (Feb. 2014) (New York, NY).

* cited by examiner

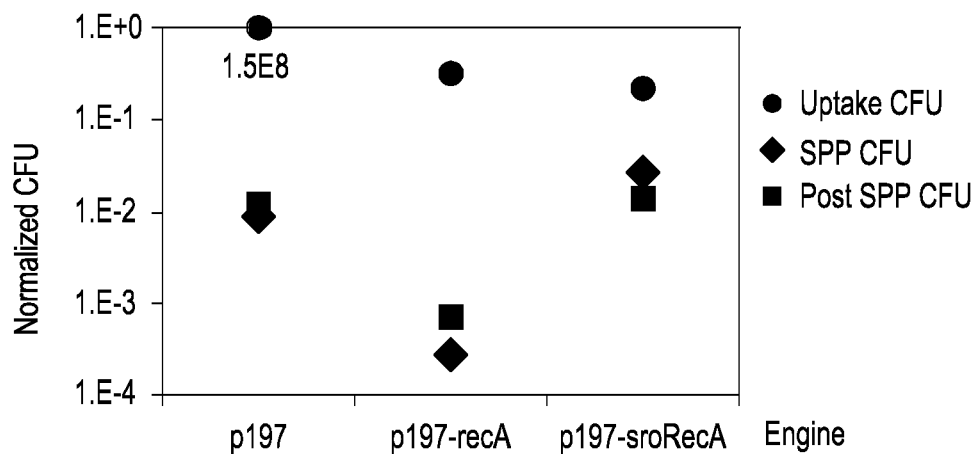
FIG. 8A
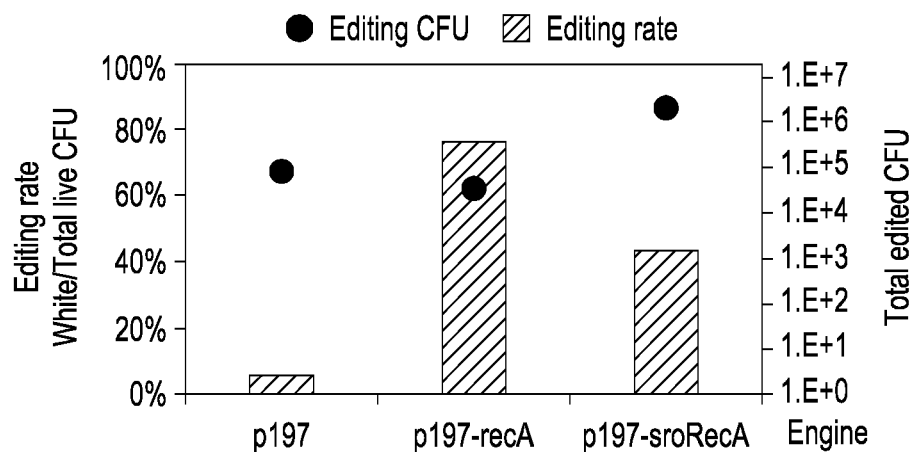
FIG. 8B
| Construct | Edit% | Post SPP survival% |
|---|---|---|
| P197 | 2/38 | 38/50 |
| P197-recA | 15/20 | 20/50 |
| P197-srpRrecA | 21/49 | 49/50 |
FIG. 8C

METHODS FOR INCREASING OBSERVED EDITING IN BACTERIA

RELATED CASES

This utility patent application is a continuation of U.S. Ser. No. 17/536,067, filed 28 Nov. 2021, now allowed; which is a continuation of U.S. Ser. No. 16/952,024, filed 18 Nov. 2020, now U.S. Pat. No. 11,203,762; which claims priority to U.S. Ser. No. 62/937,289, filed 19 Nov. 2019, entitled "Methods for Increasing Observed Editing in Bacteria."

FIELD OF THE INVENTION

The present disclosure relates to methods for increasing observed editing rates in nucleic acid-guided nuclease editing bacteria cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences, and hence gene function. These nucleases include nucleic acid-guided nucleases, which enable researchers to generate permanent edits in live cells. Of course, it is desirable to decrease the background of unedited cells so that edited cells are more readily identified.

There is thus a need in the art of nucleic acid-guided nuclease editing for improved methods, compositions, modules and instruments for increasing the percentage and diversity of edited cells in a cell population post-transformation. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Thus, presented herein is a method for nuclease-directed nuclease editing comprising: providing electrocompetent bacteria cells; providing an engine vector comprising a promoter driving expression of a coding sequence for a nucleic acid-guided nuclease; a bacterial origin of replication; a promoter driving expression of a coding sequence for a recA protein; and a selection marker; providing an editing vector comprising a promoter driving transcription of at least two editing cassettes where each editing cassette comprises a gRNA sequence and a donor DNA sequence to be transcribed; a bacterial origin of replication; and a selection marker; transforming the electrocompetent bacterial cells with the engine and editing vectors; allowing the transformed cells to edit; and pooling the edited cells or selecting small colonies of edited cells. In some aspects, the nuclease is MAD7 and in other aspects the nuclease is Cas9. In some aspects, the coding sequence for a recA protein is a coding sequence for a recA fusion protein, and in some aspects, the recA fusion protein is a recA-srpR fusion protein. In some aspects, the method further comprises the steps of, after the pooling or selecting step: making the edited bacterial cells electrocompetent; providing a second editing vector comprising a promoter driving transcription of at least two editing cassettes where each editing cassette comprises a gRNA sequence and a donor DNA sequence to be transcribed; a bacterial origin of replication; and a selection marker; transforming the electrocompetent bacterial cells with the second editing vector; allowing the transformed cells to edit; and pooling the twice-edited cells. Other embodiments provide modules and integrated instruments for processing and editing the bacterial cells, as well as compositions of matter comprising the engine and editing vectors.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 8A shows the CFUs obtained for E. coli transformed with the p197 engine vector, the p197-recA engine vector, and the p197-srpRrecA engine vector at uptake, at plating, and post-plating. FIG. 8B shows the editing CFU and percentage of triple simultaneous edits for E. coli cells transformed with the p197 engine vector, the p197-recA engine vector and the p197-srpRrecA engine vector. FIG. 8C is a table showing the percentage post-plating survival rate and the percentage editing rate for E. coli cells transformed with the p197 engine vector, the p197-recA engine vector and the p19'7-srpRrecA engine vector.

It should be understood that the drawings are not necessarily to scale, and that like reference numbers refer to like features.

DETAILED DESCRIPTION

Figure 1A:
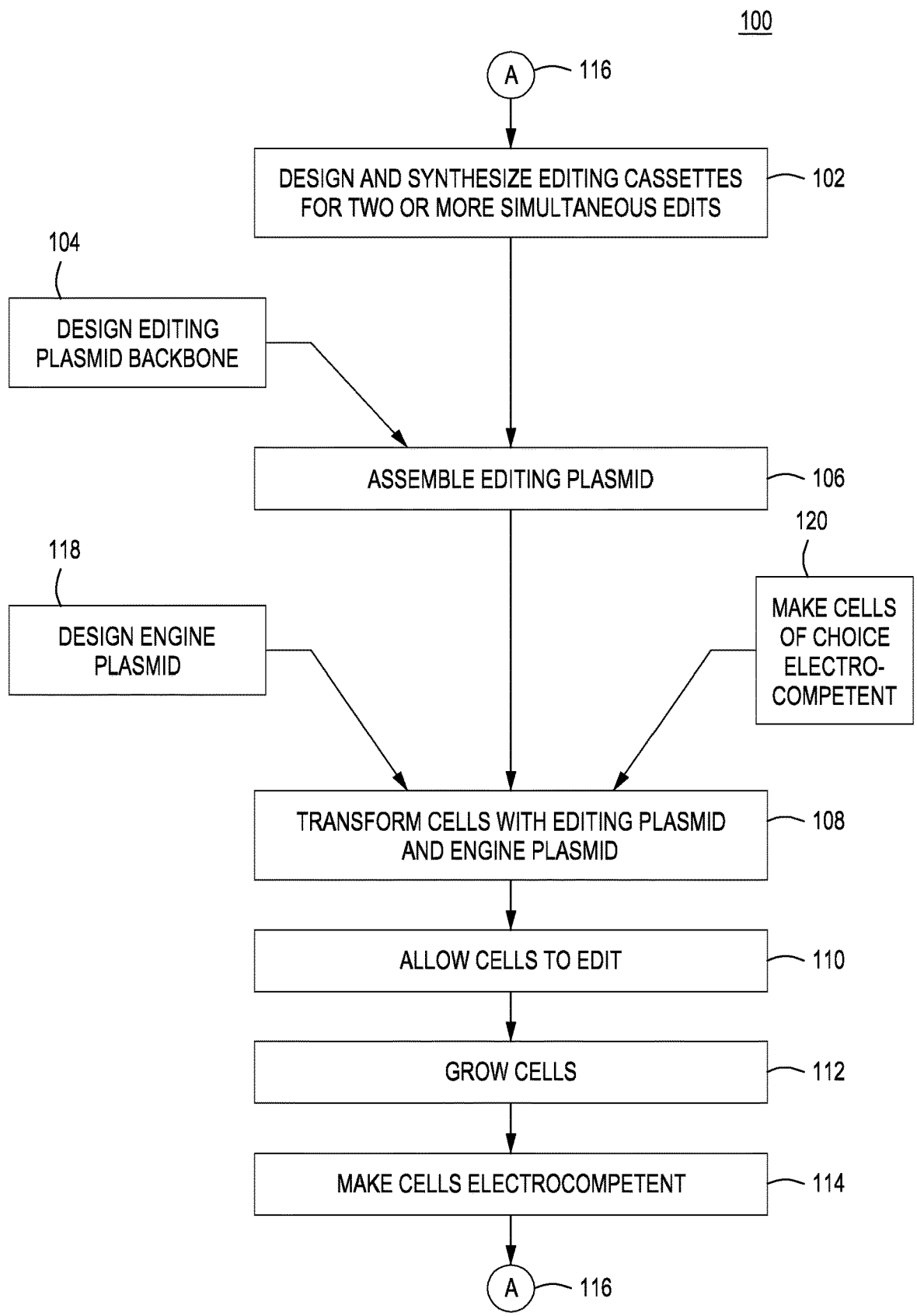
FIG. 1A is a simple process diagram for editing in bacteria cells.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); Current Protocols in Molecular Biology, Ausubel, et al. eds., (2017); Neumann, et al., *Electroporation and Electrofusion in Cell Biology*, Plenum Press, New York, 1989; and Chang, et al., Guide to Electroporation and Electrofusion, Academic Press, California (1992), all of which are herein incorporated in their entirety by reference for all purposes Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the terms "donor DNA" or "donor nucleic acid" and "homology arm" all refer to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease. In the context of this disclosure, a gRNA is linked to a capture sequence to allow for capture of the gRNA.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible.

As used herein the term "selectable marker" or "selection marker" or "survival marker" refers to a gene introduced into a cell that confers a trait suitable for artificial selection. General use selectable markers are well-known to those of ordinary skill in the art and include ampilcillin/carbenicillin, kanamycin, chloramphenicol, nourseothricin N-acetyl transferase, erythromycin, tetracycline, gentamicin, bleomycin, streptomycin, puromycin or other selectable markers that may be employed.

The term "specifically binds" as used herein includes an interaction between two molecules, e.g., a capture sequence (e.g., a poly-dT sequence) and the sequence to be captured, with a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

The terms "target genomic DNA sequence", "cellular target sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. In some embodiments, two vectors are employed comprising 1) an engine vector, comprising the coding sequence for a nucleic acid-guided nuclease and in the method and composition embodiments herein, the coding sequence for the recA protein or recA fusion protein; and 2) an editing vector, comprising at least two editing cassettes each comprising a gRNA and a donor DNA sequence. In alternative embodiments, all editing components, including the nucleic acid-guided nuclease, recA protein coding sequence, gRNA, and donor DNA sequence are all on the same vector (e.g., a combined editing/engine vector).

Nuclease-Directed Genome Editing Generally

The compositions and methods described herein are employed to perform nuclease-directed genome editing to introduce at least two simultaneous desired edits to a population of bacteria cells. In some embodiments, recursive cell editing is performed where edits are introduced in successive rounds of editing. A nucleic acid-guided nuclease complexed with an appropriate synthetic guide nucleic acid (e.g., gRNA) in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. Thus, the gRNA comprises homology to the target sequence and can be used to track the edit made to the target sequence. In certain aspects, the nuclease acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette. Methods and compositions for designing and synthesizing editing cassettes are described in U.S. Pat. Nos. 10,240,167; 10,266,849; 9,982,278; 10,351,877; 10,364,442; 10,435,715; and 10,465,207, all of which are incorporated herein in their entirety. U.S. Pat. No. 10,465,207 is drawn to multiplex editing cassettes (e.g., two or more editing cassettes targeting different regions in the genome) as used in the method embodiments employed herein. Editing cassettes, in addition to paired gRNAs and donor DNAs, may and typically do comprise additional sequences such as bar codes.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. Because of this complementarity, the gRNA sequence may serve as a proxy for the edit made. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to the cell, or in vitro. For example, the target sequence can be a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA).

The guide nucleic acid may be and preferably is part of an editing cassette that encodes the donor nucleic acid that targets a cellular target sequence. Alternatively, the guide nucleic acid may not be part of the editing cassette and instead may be encoded on the editing vector backbone. For example, a sequence coding for a guide nucleic acid can be assembled or inserted into a vector backbone first, followed by insertion of the donor nucleic acid in, e.g., an editing cassette. In other cases, the donor nucleic acid in, e.g., an editing cassette can be inserted or assembled into a vector backbone first, followed by insertion of the sequence coding for the guide nucleic acid. Preferably, the sequence encoding the guide nucleic acid and the donor nucleic acid are located together in a rationally-designed editing cassette where at least two editing cassettes in an editing vector or plasmid are simultaneously transformed into a bacteria cell.

The target sequence is associated with a proto-spacer adjacent motif (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In most embodiments, genome editing of a cellular target sequence both introduces a desired DNA change to a cellular target sequence, e.g., the genomic DNA of a cell, and removes, mutates, or renders inactive a proto-spacer adjacent motif (PAM) and/or spacer region in the cellular target sequence (e.g., renders the target site immune to further nuclease binding). Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease component of the nucleic acid-guided nuclease editing system, a polynucleotide sequence encoding the nucleic acid-guided nuclease can be codon optimized for expression in particular cell types, such as bacteria cells. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7 or other MADzymes. As with the guide nucleic acid, the nuclease is encoded by a DNA sequence on a vector and optionally is under the control of an inducible promoter. In some embodiments, the promoter may be separate from but the same as the promoter controlling transcription of the guide nucleic acid; that is, a separate promoter drives the transcription of the nuclease and guide nucleic acid sequences but the two promoters may be the same type of promoter. Alternatively, the promoter controlling expression of the nuclease may be different from the promoter controlling transcription of the guide nucleic acid; that is, e.g., the nuclease may be under the control of, e.g., the p1 promoter, and the guide nucleic acid may be under the control of the, e.g., pBAD promoter.

Another component of the nucleic acid-guided nuclease system is the donor nucleic acid (or homology arm) comprising homology to the cellular target sequence. The donor nucleic acid is on the same vector and even in the same editing cassette as the guide nucleic acid and preferably is (but not necessarily is) under the control of the same promoter as the editing gRNA (that is, a single promoter driving the transcription of both the editing gRNA and the donor nucleic acid). The donor nucleic acid is designed to serve as a template for homologous recombination with a cellular target sequence nicked or cleaved by the nuclease acid-guided nuclease as a part of the gRNA/nuclease complex; that is, the donor nucleic acid provides the desired edit in the cellular target sequence. A donor nucleic acid polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Ser. No. 16/275,465, filed 14 Feb. 2019. In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm). When optimally aligned, the donor nucleic acid overlaps with (is complementary to) the cellular target sequence by, e.g., about 20, 25, 30, 35, 40, 50, 60, 70, 80, 90 or more nucleotides. In many embodiments, the donor nucleic acid comprises two homology arms (regions complementary to the cellular target sequence) flanking the mutation or difference between the donor nucleic acid and the cellular target sequence. The donor nucleic acid comprises at least one mutation or alteration compared to the cellular target sequence, such as an insertion, deletion, modification, or any combination thereof compared to the cellular target sequence.

As described in relation to the gRNA, the donor nucleic acid is preferably provided as part of a rationally-designed editing cassette, where, in this embodiment, two of which are inserted into an editing plasmid backbone where the editing plasmid backbone may comprise a promoter to drive transcription of the editing cassettes. In the method embodiments described herein there may be more than two, e.g., three, four, or more editing gRNA/donor nucleic acid rationally-designed editing cassettes inserted into an editing vector, where each editing cassette is under the control of separate, different promoters, or each editing cassette is under the control of separate like promoters, or where all editing cassettes are under the control of a single promoter. In some embodiments the promoter driving transcription of the editing cassettes is optionally an inducible promoter.

In addition to the donor nucleic acid, an editing cassette may comprise one or more primer sites. The primer sites can be used to amplify the editing cassettes by using oligonucleotide primers; for example, if the primer sites flank one or more of the other components of the editing cassette. In addition, the editing cassettes may comprise a barcode. A barcode is a unique DNA sequence that corresponds to the donor DNA sequence such that the barcode can identify the edit made to the corresponding cellular target sequence. The barcode typically comprises four or more nucleotides and is captured to determine what edit was made in the single cell workflow. In some embodiments, the editing cassettes comprise a collection or library of editing gRNAs and of donor nucleic acids representing, e.g., gene-wide or genome-wide libraries of editing gRNAs and donor nucleic acids. The library of editing cassettes is cloned into vector backbones where, e.g., each different donor nucleic acid is associated with a different barcode. Also, in preferred embodiments, an editing vector or plasmid encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs, particularly as an element of the nuclease sequence. In some embodiments, the engineered nuclease comprises NLSs at or near the amino-terminus, NLSs at or near the carboxy-terminus, or a combination.

Increasing Observed Editing Rates of Transformed Bacteria Cells

The present disclosure is drawn to increasing the observed editing rates in bacteria cells post-editing. The present compositions and methods in combination lead to a phenomenon of "edit or die." Although less cells survive plating and editing, a large percentage of cells that do survive are multiple editors. In one experiment it was found that if a cell survives transformation, plating and editing, 75% of the surviving cells are triple editors; that is, 75% of the surviving cells were simultaneously edited with edits at three different locations within the bacterial genome.

Figure 1B:
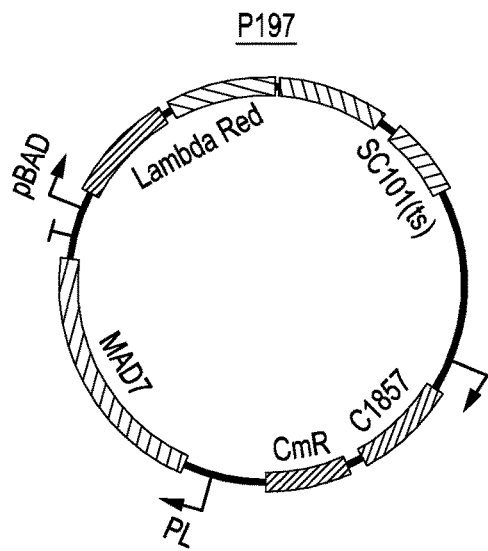
FIG. 1B is a vector map for the p197 engine vector.
Figure 1C:
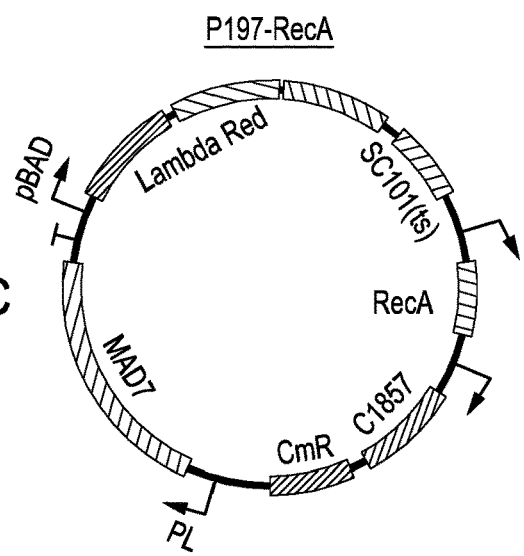
FIG. 1C is a vector map for the p197-recA engine vector.
Figure 1D:
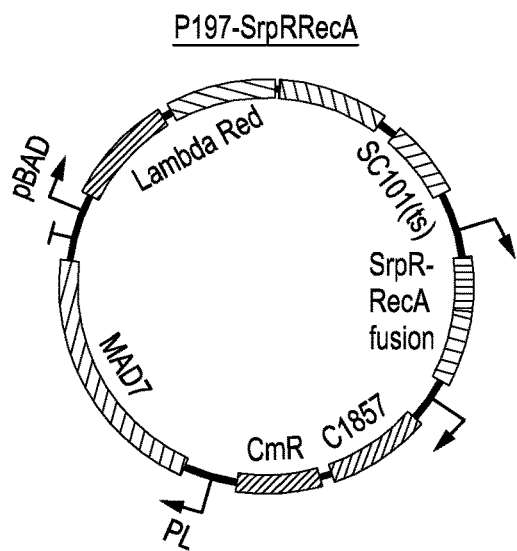
FIG. 1D is a vector map for the p197-srpRrecA engine vector.
Figure 1E:
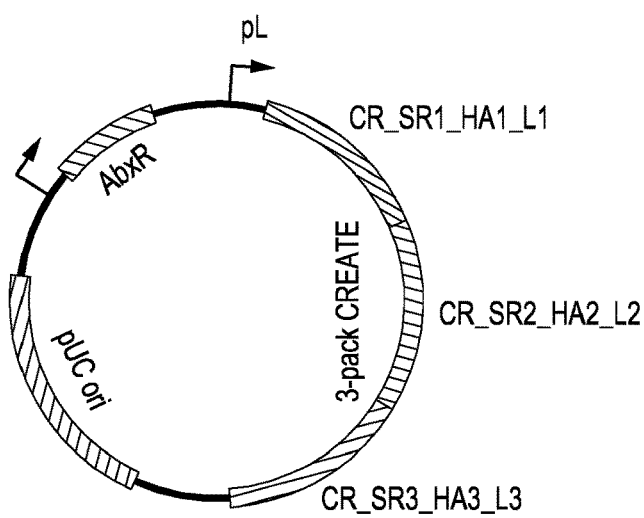
FIG. 1E is a simplified rendering of an editing plasmid having a "3-pack" multiplex or compound editing cassette.

FIG. 1A is a general flow chart for the nucleic guided-nuclease editing methods according to the present disclosure. In a first step of method 100, a library of rationally-designed editing cassettes is synthesized 102, where at least two editing cassettes targeting two different target regions in the bacterial genome are used in each editing plasmid or vector. Again, methods and compositions for designing and synthesizing editing cassettes are described in U.S. Pat. Nos. 10,240,167; 10,266,849; 9,982,278; 10,351,877; 10,364,442; 10,435,715; and 10,465,207, all of which are incorporated herein in their entirety. U.S. Pat. No. 10,465,207 is drawn to multiplex or compound editing cassettes (e.g., two or more cassettes targeting different regions in the genome) as used in the method embodiments employed herein. Once designed and synthesized, the editing cassettes are amplified and purified. One exemplary multiplex or compound editing cassette is shown in FIG. 1E.

Next or simultaneously at step 104, editing plasmid backbones are designed. The editing plasmid backbone typically comprises at least one selectable marker sequence, a bacterial origin of replication and other genetic elements. Also next or simultaneously, an engine plasmid is designed and synthesized at step 118. Exemplary engine plasmids are shown at FIGS. 1B, 1C and 1D and comprise a coding sequence for a nucleic acid-guided nuclease (e.g., a coding sequence for MAD7), the coding sequences for the components of the Red recombineering system, a bacterial origin of replication, a selectable marker sequence (e.g., typically a different selectable marker than the selectable marker that is on the editing plasmid), and, if present, a coding sequence for the recA protein or recA fusion protein.

In addition to preparing editing and engine plasmids, the bacterial cells of choice are made electrocompetent 120 for transformation. Once the bacterial cells are rendered electrocompetent 120, the cells, editing plasmids, and engine plasmids are combined and the editing plasmids and engine plasmids are transformed into (e.g., electroporated into) the cells 106. In some embodiments of the present methods, the cells are transformed simultaneously with an editing plasmid and an engine plasmid expressing the editing nuclease; alternatively, the cells may already have been transformed with an engine plasmid configured to express the nuclease. Transformation is intended to include to a variety of art-recognized techniques for introducing an exogenous nucleic acid sequence (e.g., DNA) into a target cell, and the term "transformation" as used herein includes all transformation and transfection techniques. Such methods include, but are not limited to, electroporation, lipofection, optoporation, injection, microprecipitation, microinjection, liposomes, particle bombardment, sonoporation, laser-induced poration, bead transfection, calcium phosphate or calcium chloride co-precipitation, or DEAE-dextran-mediated transfection. Additionally, hybrid techniques that exploit the capabilities of mechanical and chemical transfection methods can be used, e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, *Molecular Cloning: A Laboratory Manual,* 4th, ed., Cold Spring Harbor Laboratory Press, Cold Spring Harbor, N.Y., 2014). The present automated methods using the automated multi-module cell processing instrument utilize a flow-through electroporation such as the exemplary device shown in FIGS. 7A-7E.

Once transformed, the cells are allowed to edit 108 in the presence of selective agents that select for the engine and editing plasmids. As described above, drug selectable markers such as ampilcillin/carbenicillin, kanamycin, chloramphenicol, nourseothricin N-acetyl transferase, erythromycin, tetracycline, gentamicin, bleomycin, streptomycin, puromycin or other selectable markers may be employed.

At a next step, after editing takes place the cells are grown 112 until 1) the cells enter (or are close to entering) the stationary phase of growth and colonies become normalized or 2) until the cells form differentially-sized colonies (e.g., large and small colonies). If cells are grown until the colonies are normalized (e.g., all cells enter the stationary phase of growth), the cells will be enriched for edited cells. If the cells are grown to where differently-sized colonies are presented, small colonies can be selected where the small colonies are likely colonies arising from edited cells. See, e.g., U.S. Ser. No. 16/454,865, filed 26 Jun. 2019 and U.S. Ser. No. 16/597,831, filed 9 Oct. 2019. Once the cells are grown either to stationary phase or to differentially-sized colonies, the cells may be pooled (if from normalized colonies) or selected (if from differentially-sized colonies) and transferred to a different vessel and fresh media, then grown to a desired OD to be made electrocompetent 114 again, followed by another round of editing 116.

FIG. 1B is an exemplary engine vector map for the p197 engine vector. Beginning at approximately 10 o'clock, there is a pBAD inducible promoter driving transcription of the Red recombineering system; an SC101 bacterial origin of replication (in this instance, a temperature sensitive origin of replication); a coding sequence for the c1857 repressor gene (described below); a coding sequence for a carbenicillin resistance gene; and a pL inducible promoter driving expression of a MAD7 nuclease coding sequence. The protein product of the c1857 repressor gene on the engine vector at temperatures under 40° C. actively represses the pL promoter driving transcription of the nuclease; however, at temperatures above 40° C. the protein product of the c1857 repressor gene on the engine vector unfolds (e.g., degrades). The unfolded or degraded c1857 repressor gene protein product cannot bind the pL promoter driving expression of the nuclease and thus the pL promoter is active driving transcription of the nuclease on the engine vector at elevated temperatures.

FIG. 1C is an exemplary engine vector map for the p197-recA engine vector. Beginning at approximately 10 o'clock, there is a pBAD inducible promoter driving transcription of the Red recombineering system; an SC101 bacterial origin of replication (in this instance, a temperature sensitive origin of replication); a coding sequence for a recA protein (described below); a coding sequence for the c1857 repressor gene (described above); a coding sequence for a carbenicillin resistance gene; and a pL inducible promoter driving expression of a MAD7 nuclease coding sequence. As with the p197 engine vector described in relation to FIG. 1B, the protein product of the c1857 repressor gene on the engine vector at temperatures under 40° C. actively represses the pL promoter halting transcription of the nuclease but at temperatures above 42° C. the protein product of the c1857 repressor gene degrades and is unable to repress the pL promoter thereby allowing expression of the MAD7 nuclease. As for recA, recA is a 38 kilodalton protein that is essential for the repair and maintenance of DNA. RecA has been found to have a structural and functional homolog in every species examined. The homologous protein in eukaryotes is RAD51. In the embodiments herein, recA is used to increase DNA repair as a result of the editing process.

FIG. 1D is an exemplary engine vector map for the p197-srpRrecA engine vector. Beginning at approximately 10 o'clock, there is a pBAD inducible promoter driving transcription of the Red recombineering system; an SC101 bacterial origin of replication (in this instance, a temperature sensitive origin of replication); a coding sequence for an srpP protein coding sequence (described below) fused to a recA protein (described above); a coding sequence for the c1857 repressor gene (described above); a coding sequence for a carbenicillin resistance gene and a pL inducible promoter driving expression of a MAD7 nuclease coding sequence. As with the p197 engine vector described in relation to FIG. 1B and p197-recA vector described in relation to FIG. 1C, the protein product of the c1857 repressor gene on the engine vector at temperatures under 40° C. actively represses the pL promoter halting transcription of the nuclease but at temperatures above 42° C. the protein product of the c1857 repressor gene degrades thereby allowing expression of the MAD7 nuclease. As for recA, as described above, recA is a protein essential for the repair and maintenance of DNA. In the p197-recAsrpR engine vector, the recA coding sequence is fused to an srpR coding sequence via an 18-bp linker sequence. The stop codon (TAA) of the srpR coding sequence was removed to create an in-frame fusion protein comprising the last amino acid (glutamate) of the srpR protein at the N-terminal portion and the first amino acid (methionine) of the recA protein. The srpR protein is a DNA binding protein originally isolated from *Pseudomonas putida*, and putatively encodes a TetR family repressor with strong DNA binding affinity (see, e.g., Stanton, et al., "Genomic mining of prokaryotic repressors for orthogonal logic gates", Nat. Chem. Biol., 10:99-105 (2014)).

In addition to one of the engine plasmids described in relation to FIGS. 1B-1D, an editing plasmid is also transformed into the bacteria cells of interest. As described above, the editing plasmid comprises at least two gRNA/donor DNA (homology arm) pairs targeting two different target regions in the bacterial genome; and in one exemplary editing plasmid as depicted in FIG. 1E, the editing plasmid comprises three gRNA/donor DNA (homology arm) pairs targeting three different target regions in the bacterial genome. Again, methods and compositions for designing and synthesizing editing cassettes are described in U.S. Pat. Nos. 10,240,167; 10,266,849; 9,982,278; 10,351,877; 10,364,442; 10,435,715; and 10,465,207, all of which are incorporated herein in their entirety; where U.S. Pat. No. 10,465,207 is drawn to multiplex or compound editing cassettes (e.g., two or more cassettes targeting different regions in the genome) as used in the method embodiments employed herein. Looking at FIG. 1E, beginning at approximately 10 o'clock, there is a promoter driving expression of a selection marker (e.g., antibiotic resistance gene, and preferably not the same antibiotic resistance gene as is located on the engine plasmid); a pL inducible promoter driving expression of the three editing cassettes (e.g., CR-SR1-HA1-L1; CR-SR2-HA2-L2; and CR-SR3-HA3-L3) (the p1 promoter and control thereof by the c1857 repressor gene on the engine vector is described above); and a bacterial origin of replication. The components of the editing cassettes include "CR", which is the portion of the gRNA corresponding to the CRISPR structure sequence for the MAD7 nuclease, where each editing cassette comprises the same or very similar CR sequence; "SR", which is the target-specific spacer region of the gRNA and is different for each editing cassette in this example; "HA", which is the homology arm or donor DNA component and is different for each editing cassette in this example; and "L", which is a linker sequence that is different for each editing cassette and in this example is used in assembly of the multiplex (e.g., compound) editing cassette.

Figure 2A:
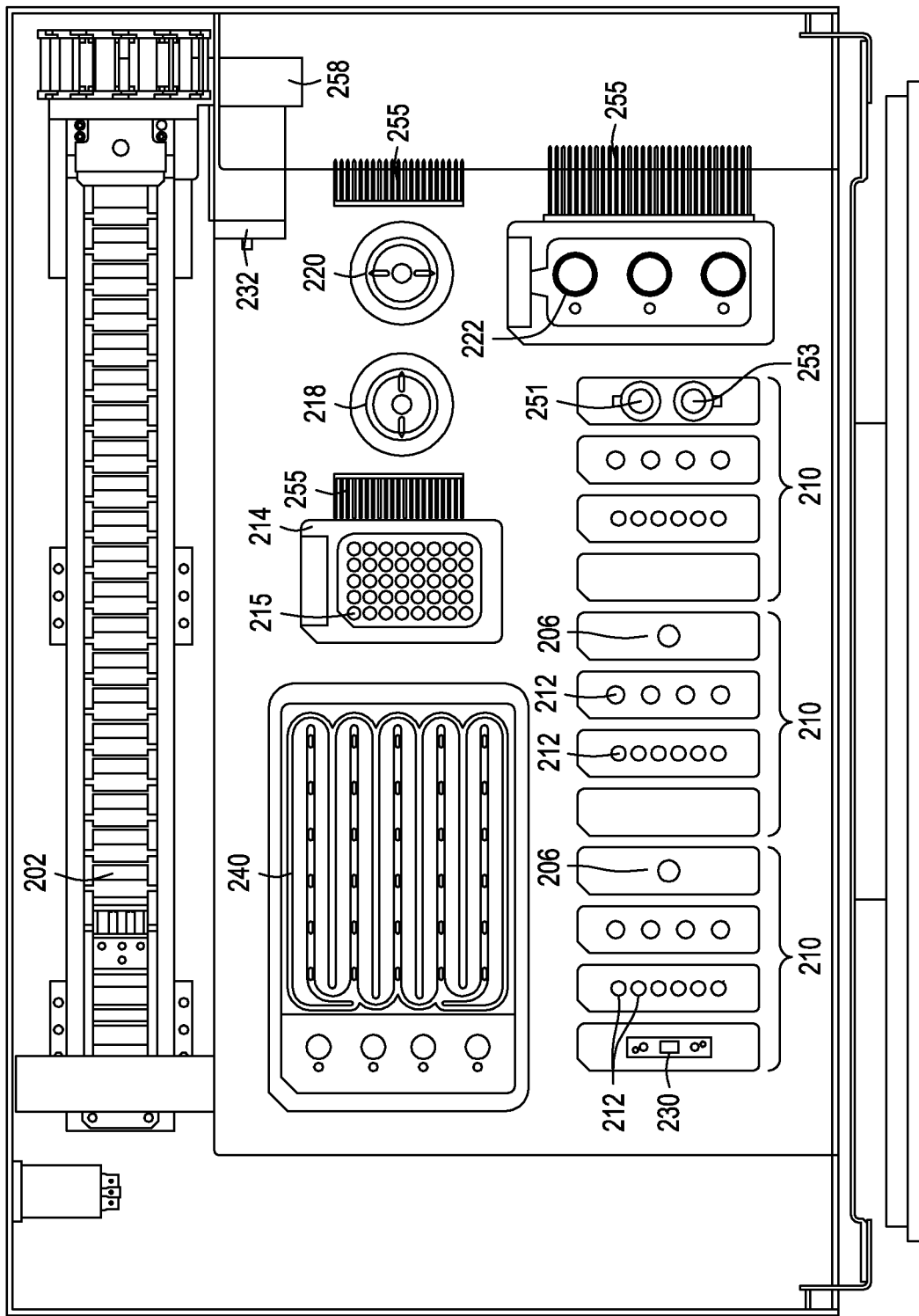
FIGS. 2A-2C depict three different views of an exemplary automated multi-module cell processing instrument for performing nucleic acid-guided nuclease editing employing a split nuclease tethering system.

Automated Cell Editing Instruments and Modules to Perform Nucleic Acid-Guided Nuclease Editing in Cells
Automated Cell Editing Instruments FIG. 2A depicts an exemplary automated multi-module cell processing instrument 200 to, e.g., perform rationally-designed genome edits in bacteria as described herein. The instrument 200, for example, may be and preferably is designed as a stand-alone desktop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 comprising reservoirs 212 and transformation module 230 (e.g., a flow-through electroporation device as described in detail in relation to FIGS. 5B-5F), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge 210 and wash cartridge 204 may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, NV (see, e.g., WO2018015544A1), or Beckman Coulter, Inc. of Fort Collins, CO. (see, e.g., US20160018427A1). Pipette tips may be provided in a pipette transfer tip supply (not shown) for use with the air displacement pipettor 232.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises two cell growth vials 218, 220 (described in greater detail below in relation to FIGS. 3A-3D). Additionally seen is the TFF module 222 (described above in detail in relation to FIGS. 4A-4E). Also illustrated as part of the automated multi-module cell processing instrument 200 of FIG. 2A is a singulation module 240 (e.g., a solid wall isolation, incubation and normalization device (SWIIN device) is shown here) described herein in relation to FIGS. 6B-6E, served by, e.g., robotic liquid handing system 258 and air displacement pipettor 232. Also note the placement of three heatsinks 255.

Figure 2B:
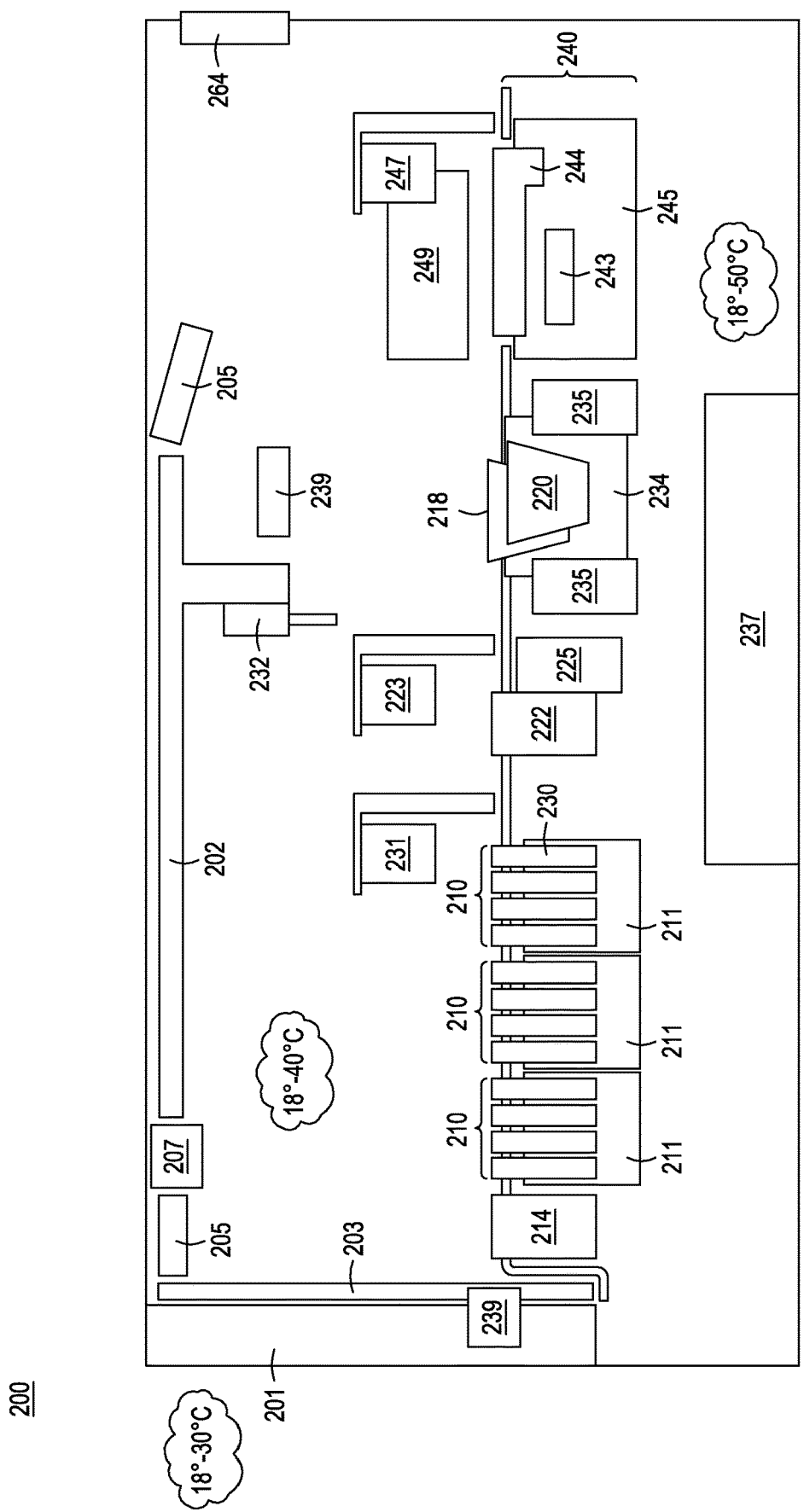

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232. The deck of the multi-module cell processing instrument 200 may include a protection sink such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 233. Thermal assemblies 225, 235, and 245 encompass thermal electric devices such as Peltier devices, as well as heatsinks, fans and coolers. The two rotating growth vials 218 and 220 are within a growth module 234, where the growth module is served by two thermal assemblies 235. Also seen is the SWIIN module 240, comprising a SWIIN cartridge 241, where the SWIIN module also comprises a thermal assembly 245, illumination 243 (in this embodiment, backlighting), evaporation and condensation control 249, and where the SWIIN module is served by SWIIN interface (e.g., manifold arm) and actuator 247.

Also seen in this view is touch screen display 201, display actuator 203, illumination 205 (one on either side of multi-module cell processing instrument 200), and cameras 239 (one illumination device on either side of multi-module cell processing instrument 200). Finally, element 237 comprises electronics, such as circuit control boards, high-voltage amplifiers, power supplies, and power entry; as well as pneumatics, such as pumps, valves and sensors.

Figure 2C:
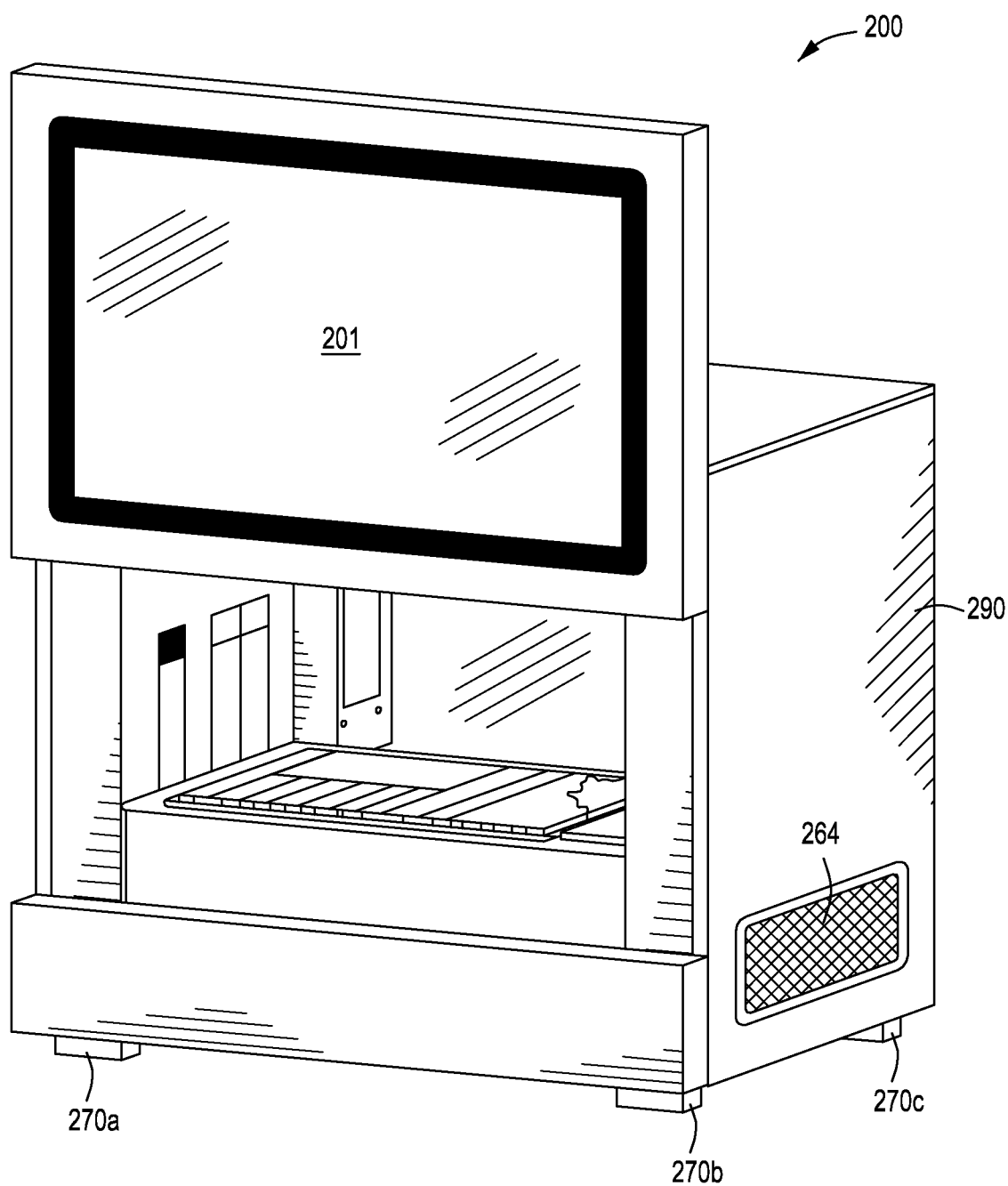

FIG. 2C illustrates a front perspective (door open) view of multi-module cell processing instrument 200 in a desktop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device, one or more rotating growth vials 218, 220 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316, issued 9 Apr. 2019; U.S. Pat. No. 10,329,559, issued 25 Jun. 2019; and U.S. Pat. No. 10,323,242, issued 18 Jun. 2019; U.S. Pat. No. 10,421,959, issued 24 Sep. 2019; and Ser. No. 16/412,195, filed 14 May 2019; and Ser. No. 16/423,289, filed 28 May 2019, all of which are herein incorporated by reference in their entirety.

The Rotating Cell Growth Module

Figure 3A:
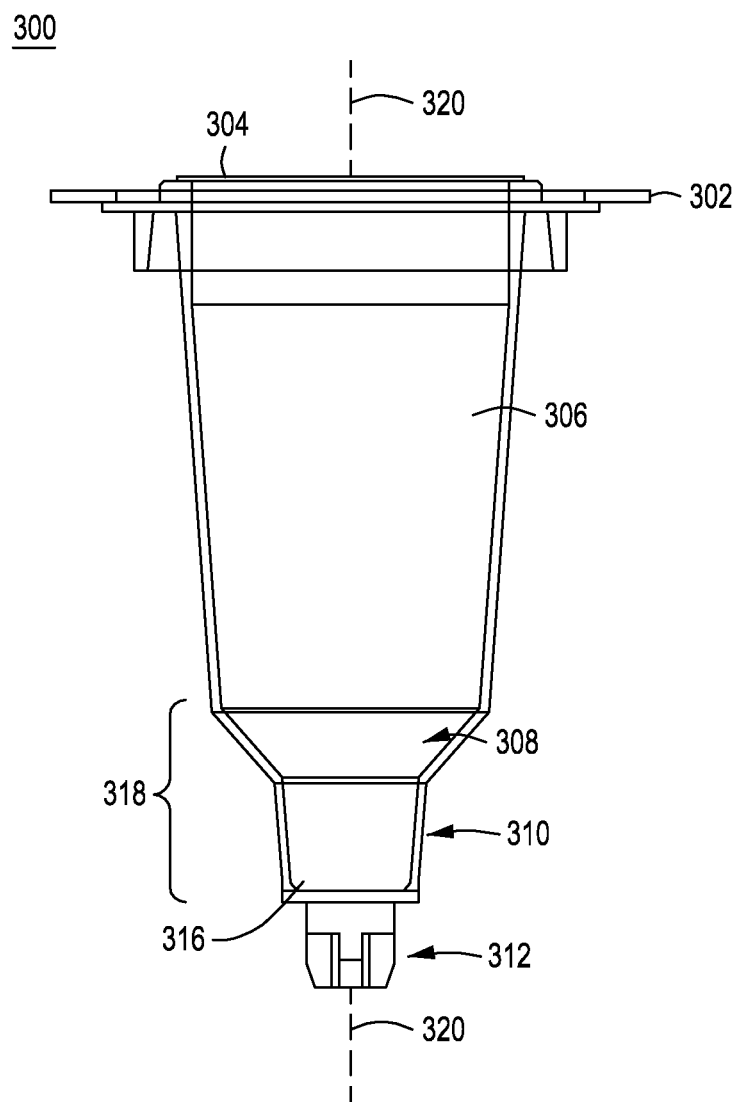
FIG. 3A depicts one embodiment of a rotating growth vial for use with the cell growth module described herein and in relation to FIGS. 3B-3D.

FIG. 3A shows one embodiment of a rotating growth vial 300 for use with the cell growth device and in the automated multi-module cell processing instruments described herein. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for sensitive measurement of OD values when the OD values of the cell culture in the vial are at a high level (e.g., later in the cell growth process), whereas the second light path 308 allows for sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 400 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 402 to overlap and engage with the cell growth device. In automated systems, the rotating growth vial 400 may be tagged with a barcode or other identifying means that can be read by a scanner or camera (not shown) that is part of the automated system.

The volume of the rotating growth vial 300 and the volume of the cell culture (including growth medium) may vary greatly, but the volume of the rotating growth vial 300 must be large enough to generate a specified total number of cells. In practice, the volume of the rotating growth vial 400 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 400. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 300 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
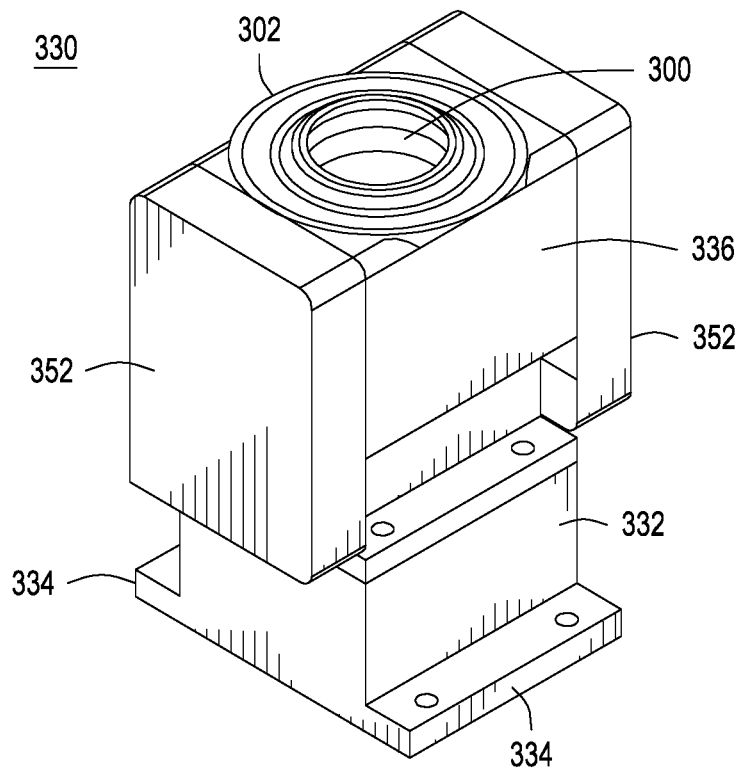
FIG. 3B illustrates a perspective view of one embodiment of a rotating growth vial in a cell growth module housing.
Figure 3C:
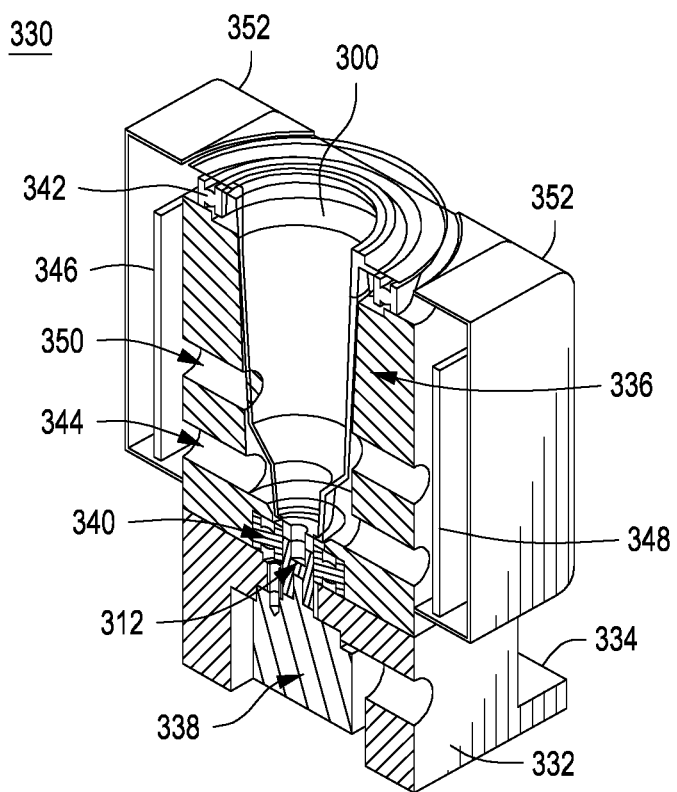
FIG. 3C depicts a cut-away view of the cell growth module from FIG. 3B.

FIG. 3B is a perspective view of one embodiment of a cell growth device 330. FIG. 3C depicts a cut-away view of the cell growth device 330 from FIG. 3B. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3C depicts additional detail. In FIG. 3C, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C comprises two light paths: a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3C but may be seen in FIG. 3A. In addition to light paths 344 and 340, there is an emission board 348 to illuminate the light path(s), and detector board 346 to detect the light after the light travels through the cell culture liquid in the rotating growth vial 300.

The motor 338 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

The processor (not shown) of the cell growth device 330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 330—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 330, where the second spectrophotometer is used to read a blank at designated intervals.

Figure 3D:
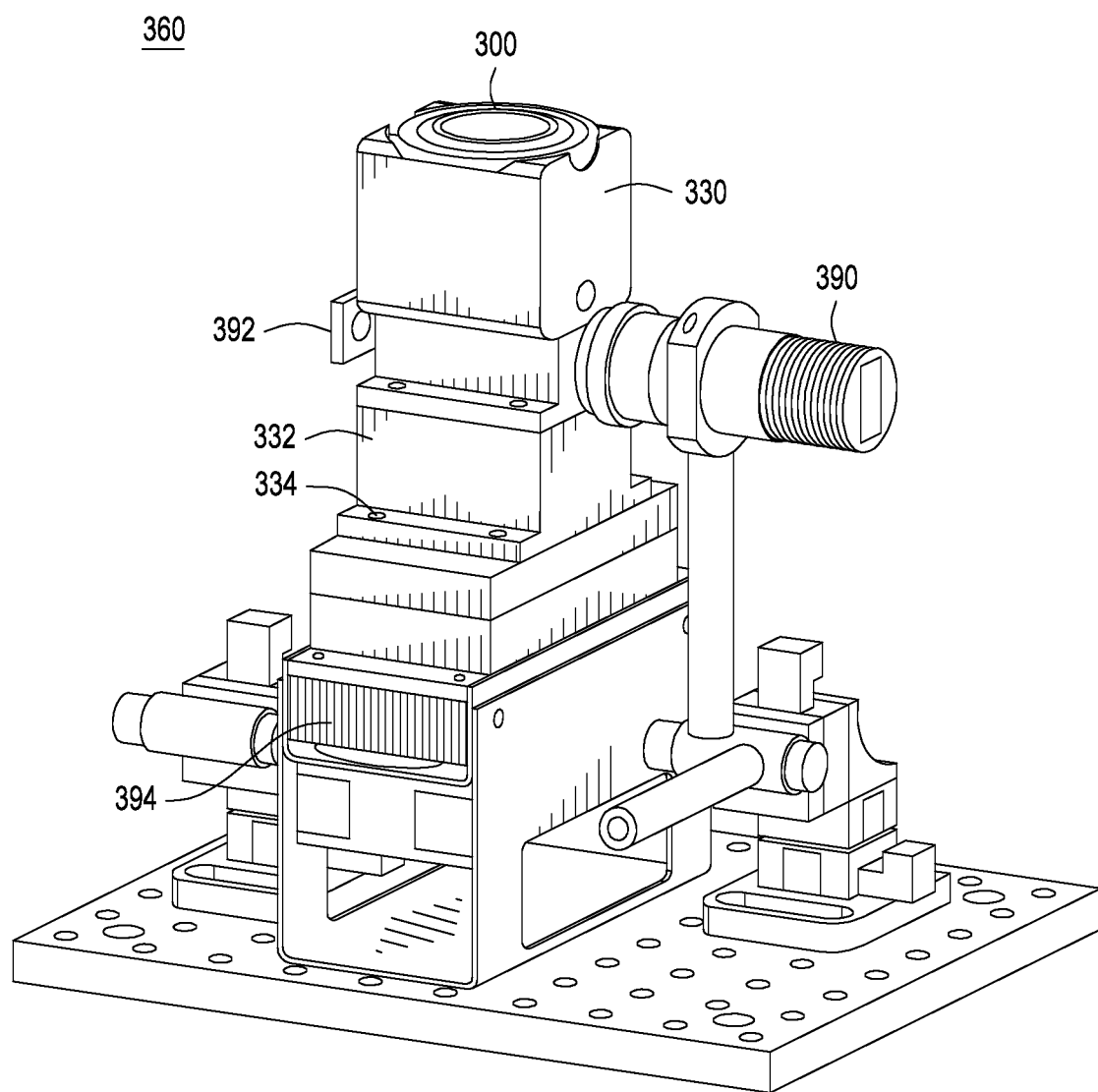
FIG. 3D illustrates the cell growth module of FIG. 3B coupled to LED, detector, and temperature regulating components.

FIG. 3D illustrates a cell growth device 330 as part of an assembly comprising the cell growth device 330 of FIG. 3B coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 330 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 430 may include additional sensors for measuring, e.g., dissolved oxygen, carbon dioxide, pH, conductivity, and the like. For additional details regarding rotating growth vials and cell growth devices see U.S. Pat. No. 10,435,662, issued 8 Oct. 2019; and U.S. Pat. No. 10,443,031, issued 15 Oct. 2019; and U.S. Ser. No. 16/552,981, filed 27 Aug. 2019.

The Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one subcomponent or module that is desired in cell processing systems for the processes listed above is a module or component that can grow, perform buffer exchange, and/or concentrate cells and render them competent so that they may be transformed or transfected with the nucleic acids needed for engineering or editing the cell's genome.

Figure 4A:
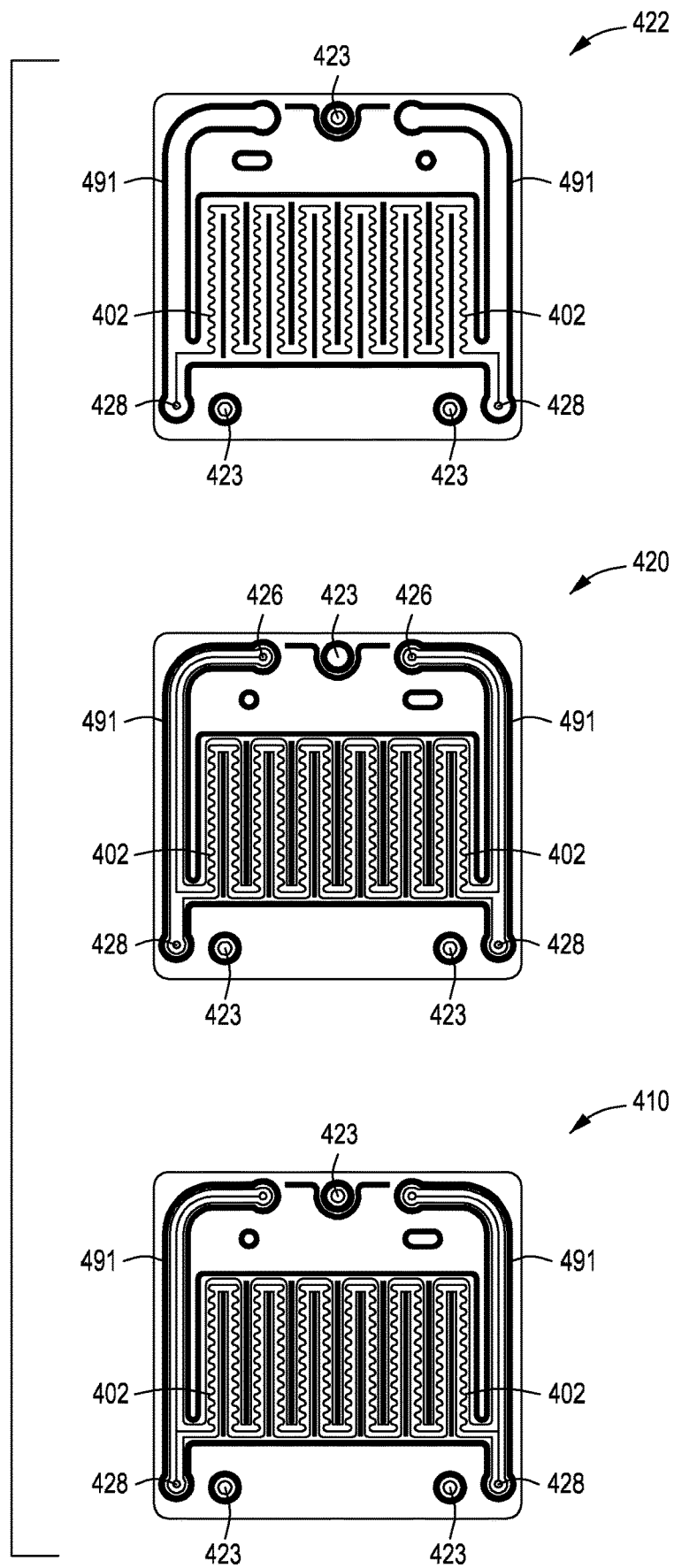
FIG. 4A depicts retentate (top) and permeate (center) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top center of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

At bottom of FIG. 4A is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 102 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

Figure 4B:
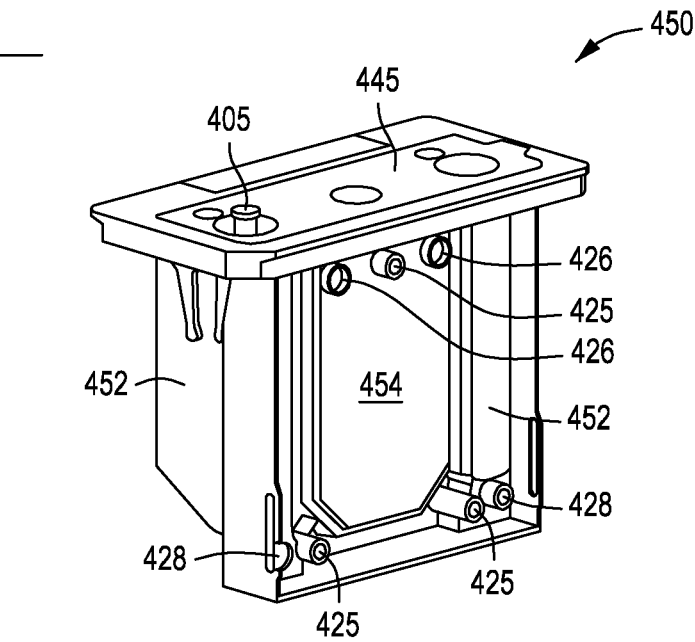
FIG. 4B depicts two side perspective views of a reservoir assembly of a tangential flow filtration module.
Figure 4B:
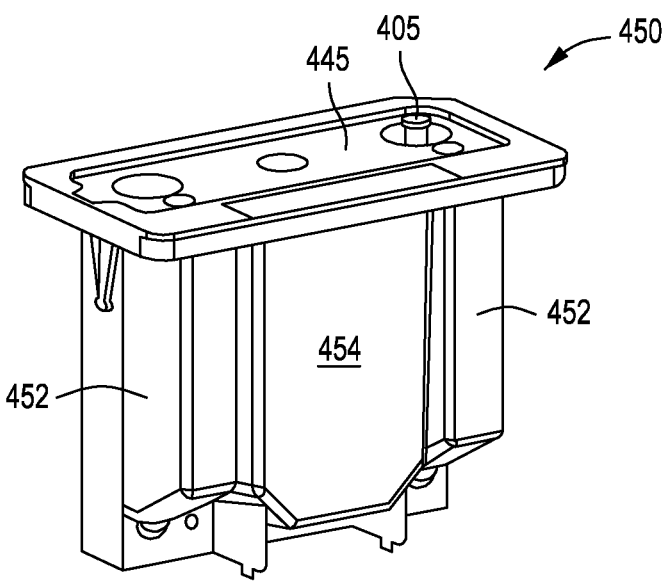

FIG. 4B shows front perspective (right) and rear perspective (left) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E. At left in FIG. 4B is a rear perspective view of reservoir assembly 1250, where "rear" is the side of reservoir assembly 450 that is not coupled to the tangential flow assembly. Seen are retentate reservoirs 452, permeate reservoir 454, and gasket 445.

The TFF device (e.g., either the tangential flow filtration assembly, reservoir assembly, or both) may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
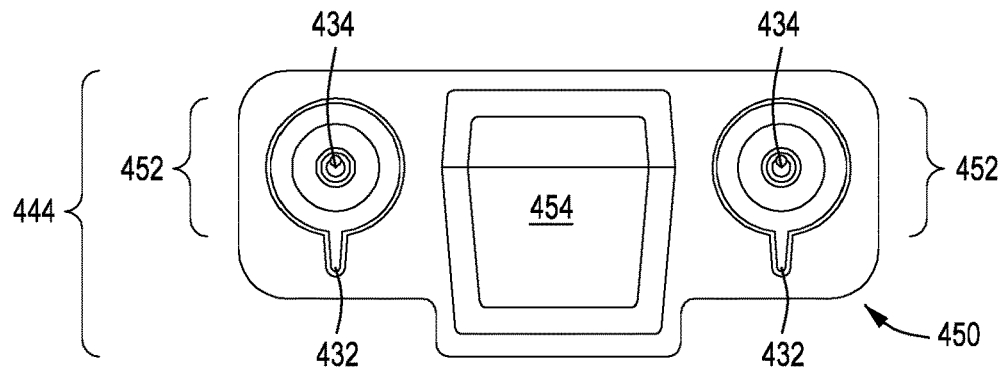
FIGS. 4C-4E depict an exemplary top, with fluidic and pneumatic ports and gasket suitable for the reservoir assemblies shown in FIG. 4B.
Figure 4D:
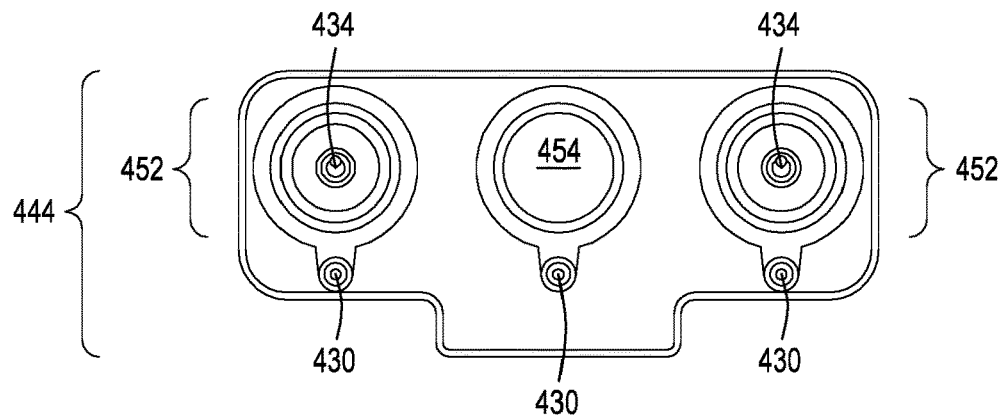
Figure 4E:
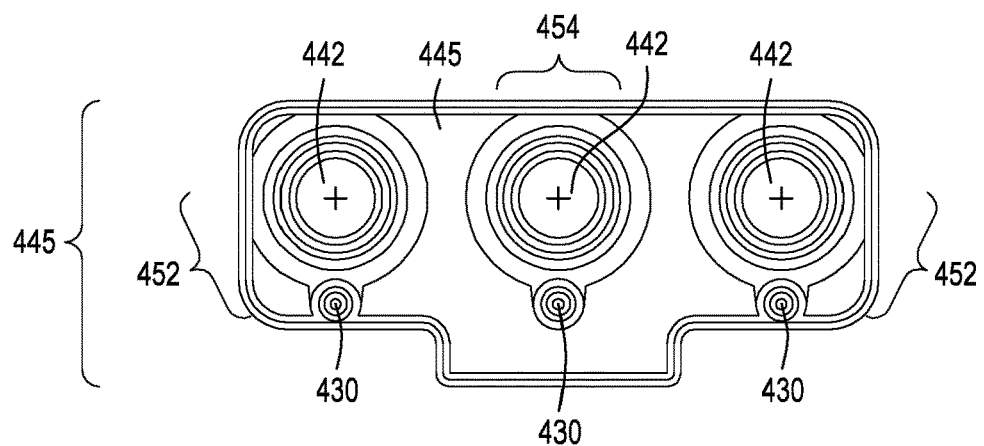

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configures to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 406, collecting the cell culture through a second retentate port 404 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicone photodiode. Generally, optical density is shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the TFF device OD measurement records the overall power transmission, so as the cells grow and become denser in population, the OD (the loss of signal) increases.

The OD system is pre-calibrated against OD standards with these values stored in an on-board memory accessible by the measurement program.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 406. Alternatively, cells can be grown in one reservoir with bubbling or agitation without passing the cells through the TFF channel from one reservoir to the other.

The overall work flow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 404, and the medium/buffer that has passed through the membrane is collected through one or both of the permeate/filtrate ports 406. All types of prokaryotic and eukaryotic cells—both adherent and non-adherent cells—can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as in this case bacteria cells; thus, LB or SOC media may be used, and the media may be provided in a reagent cartridge as part of a kit.

In both the cell growth and concentration processes, passing the cell sample through the TFF device and collecting the cells in one of the retentate ports 404 while collecting the medium in one of the permeate/filtrate ports 406 is considered "one pass" of the cell sample. The transfer between retentate reservoirs "flips" the culture. The retentate and permeate ports collecting the cells and medium, respectively, for a given pass reside on the same end of TFF device/module with fluidic connections arranged so that there are two distinct flow layers for the retentate and permeate/filtrate sides, but if the retentate port 404 resides on the retentate member of device/module (that is, the cells are driven through the channel above the membrane and the filtrate (medium) passes to the portion of the channel below the membrane), the permeate/filtrate port 406 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 404 and into the retentate reservoir (not shown). To initiate another "pass", the cell sample is passed again through the TFF device, this time in a flow direction that is reversed from the first pass. The cell sample is collected by passing through the retentate port 404 and into retentate reservoir (not shown) on the opposite end of the device/module from the retentate port 404 that was used to collect cells during the first pass. Likewise, the medium/buffer that passes through the membrane on the second pass is collected through the permeate port 406 on the opposite end of the device/module from the permeate port 406 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/561,701, filed 5 Sep. 2019.

The Cell Transformation Module

Figure 5C:
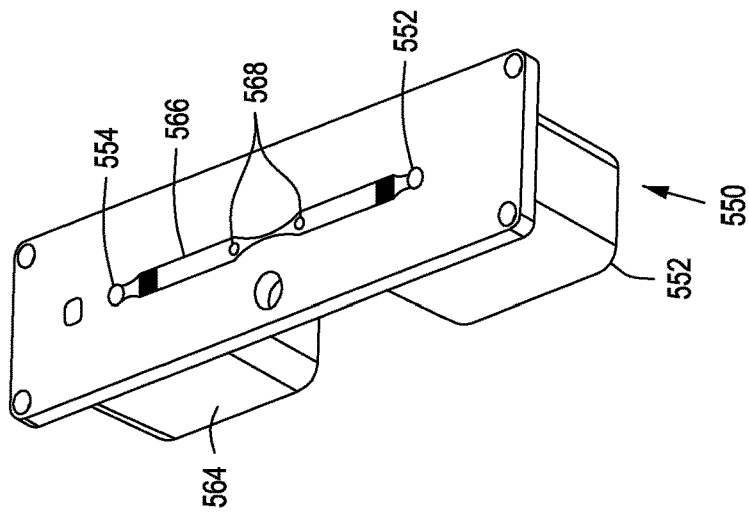
FIG. 5C depicts a bottom perspective view of one embodiment of an exemplary flow-through electroporation device that may be part of a reagent cartridge.
Figure 5B:
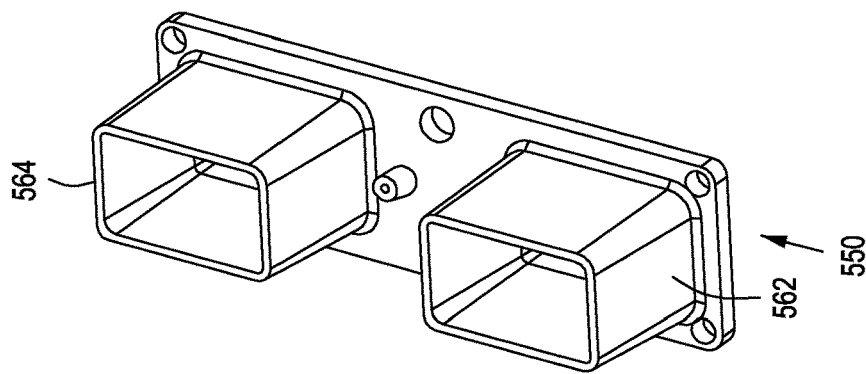
FIG. 5B is a top perspective view of one embodiment of an exemplary flow-through electroporation device that may be part of a reagent cartridge.
Figure 5A:
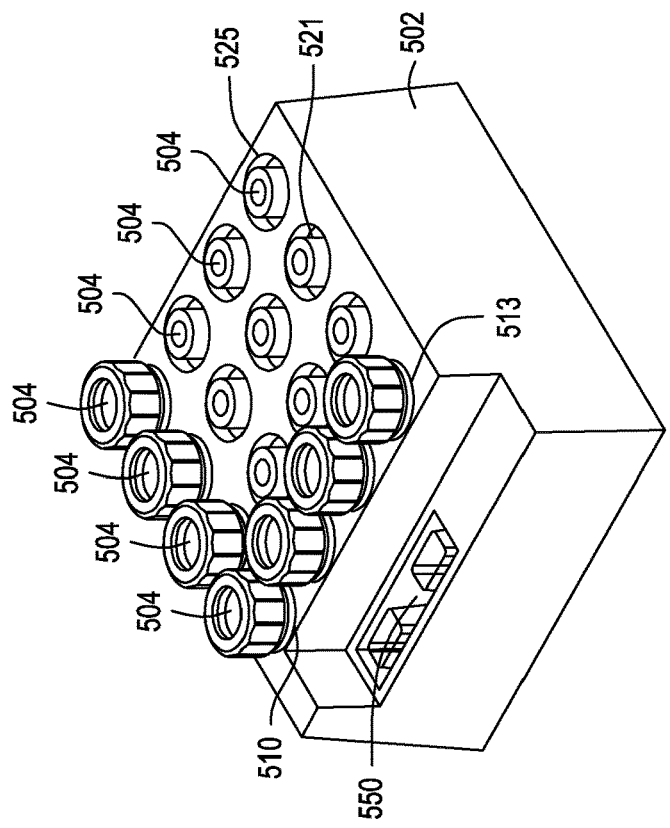
FIG. 5A depicts an exemplary combination reagent cartridge and electroporation device (e.g., transformation module) that may be used in a multi-module cell processing instrument.

FIG. 5A depicts an exemplary combination reagent cartridge and electroporation device 500 ("cartridge") that may be used in an automated multi-module cell processing instrument along with the TFF module to effect efficient editing in bacteria. In addition, in certain embodiments the material used to fabricate the cartridge is thermally-conductive, as in certain embodiments the cartridge 500 contacts a thermal device (not shown), such as a Peltier device or thermoelectric cooler, that heats or cools reagents in the reagent reservoirs or reservoirs 504. Reagent reservoirs or reservoirs 504 may be reservoirs into which individual tubes of reagents are inserted as shown in FIG. 5A, or the reagent reservoirs may hold the reagents without inserted tubes. Additionally, the reservoirs in a reagent cartridge may be configured for any combination of tubes, co-joined tubes, and direct-fill of reagents.

In one embodiment, the reagent reservoirs or reservoirs 504 of reagent cartridge 500 are configured to hold various size tubes, including, e.g., 250 ml tubes, 25 ml tubes, 10 ml tubes, 5 ml tubes, and Eppendorf or microcentrifuge tubes. In yet another embodiment, all reservoirs may be configured to hold the same size tube, e.g., 5 ml tubes, and reservoir inserts may be used to accommodate smaller tubes in the reagent reservoir. In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing instrument. As one of ordinary skill in the art will appreciate given the present disclosure, the reagents contained in the reagent cartridge will vary depending on work flow; that is, the reagents will vary depending on the processes to which the cells are subjected in the automated multi-module cell processing instrument, e.g., protein production, cell transformation and culture, cell editing, etc.

Reagents such as cell samples, enzymes, buffers, nucleic acid vectors, expression cassettes, proteins or peptides, reaction components (such as, e.g., $MgCl_2$, dNTPs, nucleic acid assembly reagents, gap repair reagents, and the like), wash solutions, ethanol, and magnetic beads for nucleic acid purification and isolation, etc. may be positioned in the reagent cartridge at a known position. In some embodiments of cartridge 500, the cartridge comprises a script (not shown) readable by a processor (not shown) for dispensing the reagents. Also, the cartridge 500 as one component in an automated multi-module cell processing instrument may comprise a script specifying two, three, four, five, ten or more processes to be performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components/modules of the automated multi-module cell processing instrument or system may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument, or, e.g., reagents for protein expression and a script that specifies the process steps for performing protein expression in an automated multi-module cell processing instrument.

For example, the reagent cartridge may comprise a script to pipette competent cells from a reservoir, transfer the cells to a transformation module, pipette a nucleic acid solution comprising a vector with expression cassette from another reservoir in the reagent cartridge, transfer the nucleic acid solution to the transformation module, initiate the transformation process for a specified time, then move the transformed cells to yet another reservoir in the reagent cassette or to another module such as a cell growth module in the automated multi-module cell processing instrument. In another example, the reagent cartridge may comprise a script to transfer a nucleic acid solution comprising a vector from a reservoir in the reagent cassette, nucleic acid solution comprising editing oligonucleotide cassettes in a reservoir in the reagent cassette, and a nucleic acid assembly mix from another reservoir to the nucleic acid assembly/desalting module, if present. The script may also specify process steps performed by other modules in the automated multi-module cell processing instrument. For example, the script may specify that the nucleic acid assembly/desalting reservoir be heated to 50° C. for 30 min to generate an assembled product; and desalting and resuspension of the assembled product via magnetic bead-based nucleic acid purification involving a series of pipette transfers and mixing of magnetic beads, ethanol wash, and buffer.

As described in relation to FIGS. 5B and 5C below, the exemplary reagent cartridges for use in the automated multi-module cell processing instruments may include one or more electroporation devices, preferably flow-through electroporation (FTEP) devices. In yet other embodiments, the reagent cartridge is separate from the transformation module. Electroporation is a widely-used method for permeabilization of cell membranes that works by temporarily generating pores in the cell membranes with electrical stimulation. Applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. In traditional electroporation devices, the cells and material to be electroporated into the cells (collectively "the cell sample") are placed in a cuvette embedded with two flat electrodes for electrical discharge. For example, Bio-Rad (Hercules, Calif.) makes the GENE PULSER XCELL™ line of products to electroporate cells in cuvettes. Traditionally, electroporation requires high field strength; however, the flow-through electroporation devices included in the reagent cartridges achieve high efficiency cell electroporation with low toxicity. The reagent cartridges of the disclosure allow for particularly easy integration with robotic liquid handling instrumentation that is typically used in automated instruments and systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, CO), etc.

FIGS. 5B and 5C are top perspective and bottom perspective views, respectively, of an exemplary FTEP device 550 that may be part of (e.g., a component in) reagent cartridge 500 in FIG. 5A or may be a stand-alone module; that is, not a part of a reagent cartridge or other module. FIG. 5B depicts an FTEP device 550. The FTEP device 550 has wells that define cell sample inlets 552 and cell sample outlets 554. FIG. 5C is a bottom perspective view of the FTEP device 550 of FIG. 5B. An inlet well 552 and an outlet well 554 can be seen in this view. Also seen in FIG. 5C are the bottom of an inlet 562 corresponding to well 552, the bottom of an outlet 564 corresponding to the outlet well 554, the bottom of a defined flow channel 566 and the bottom of two electrodes 568 on either side of flow channel 566. The FTEP devices may comprise push-pull pneumatic means to allow multi-pass electroporation procedures; that is, cells to electroporated may be "pulled" from the inlet toward the outlet for one pass of electroporation, then be "pushed" from the outlet end of the FTEP device toward the inlet end to pass between the electrodes again for another pass of electroporation. Further, this process may be repeated one to many times. For additional information regarding FTEP devices, see, e.g., U.S. Pat. No. 10,435,713, issued 8 Oct. 2019; U.S. Pat. No. 10,443,074, issued 15 Oct. 2019; U.S. Pat. No. 10,415,258, issued 17 Sep. 2019; and U.S. Pat. No. 10,323,258, issued 18 Jun. 2019. Further, other embodiments of the reagent cartridge may provide or accommodate electroporation devices that are not configured as FTEP devices, such as those described in U.S. Ser. No. 16/109,156, filed 22 Aug. 2018. For reagent cartridges useful in the present automated multi-module cell processing instruments, see, e.g., U.S. Pat. No. 10,376,889, issued 13 Aug. 2019; and U.S. Pat. No. 16,451,601, filed 25 Jun. 2019.

Figure 5D:
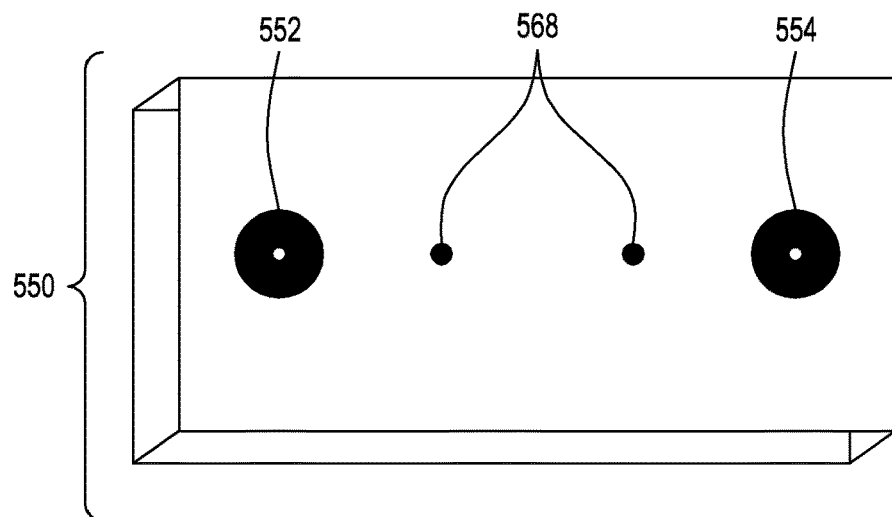
FIGS. 5D-5F depict a top perspective view, a top view of a cross section, and a side perspective view of a cross section of an FTEP device useful in a multi-module automated cell processing instrument such as that shown in FIGS. 2A-2C.
Figure 5E:
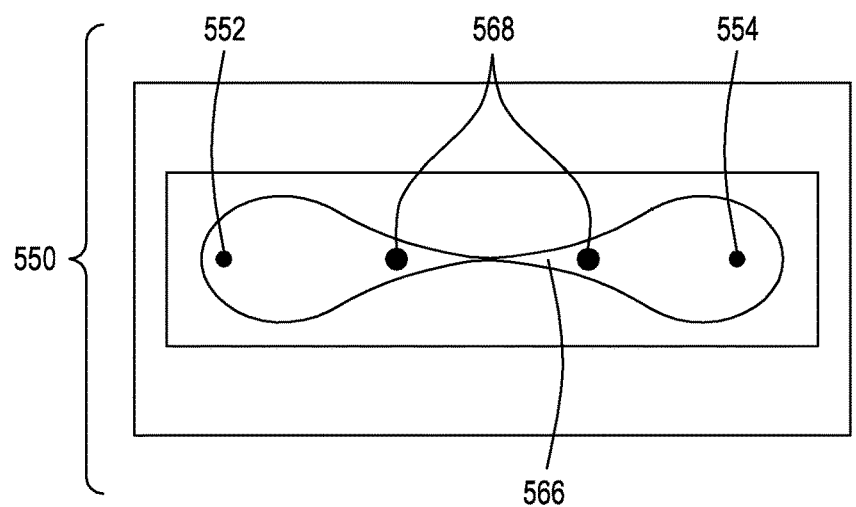
Figure 5F:
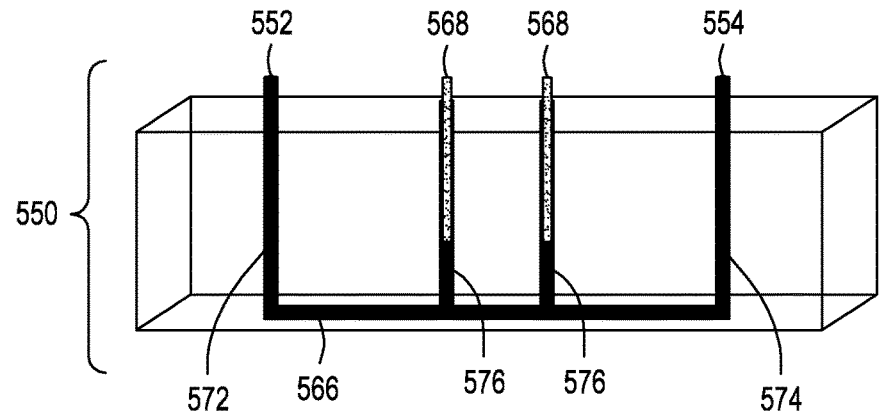

Additional details of the FTEP devices are illustrated in FIGS. 5D-5F. Note that in the FTEP devices in FIGS. 5D-5F the electrodes are placed such that a first electrode is placed between an inlet and a narrowed region of the flow channel, and the second electrode is placed between the narrowed region of the flow channel and an outlet. FIG. 5D shows a top planar view of an FTEP device 550 having an inlet 552 for introducing a fluid containing cells and exogenous material into FTEP device 550 and an outlet 554 for removing the transformed cells from the FTEP following electroporation. The electrodes 568 are introduced through channels (not shown) in the device. FIG. 5E shows a cutaway view from the top of the FTEP device 550, with the inlet 552, outlet 554, and electrodes 568 positioned with respect to a flow channel 566. FIG. 5F shows a side cutaway view of FTEP device 550 with the inlet 552 and inlet channel 572, and outlet 554 and outlet channel 574. The electrodes 568 are positioned in electrode channels 576 so that they are in fluid communication with the flow channel 566, but not directly in the path of the cells traveling through the flow channel 566. Note that the first electrode is placed between the inlet and the narrowed region of the flow channel, and the second electrode is placed between the narrowed region of the flow channel and the outlet. The electrodes 568 in this aspect of the device are positioned in the electrode channels 576 which are generally perpendicular to the flow channel 566 such that the fluid containing the cells and exogenous material flows from the inlet channel 572 through the flow channel 566 to the outlet channel 574, and in the process fluid flows into the electrode channels 376 to be in contact with the electrodes 568. In this aspect, the inlet channel, outlet channel and electrode channels all originate from the same planar side of the device. In certain aspects, however, the electrodes may be introduced from a different planar side of the FTEP device than the inlet and outlet channels.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretherketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretherketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 408 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

As mentioned, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, where the flow channel decreases in width, the flow channel may narrow to between 10 μm and 5 mm, or between 25 μm and 3 mm, or between 50 μm and 2 mm, or between 75 μm and 1 mm. The distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is wide enough so that at least two cells can fit in the narrowed portion side-by-side. For example, a typical bacterial cell is 1 μm in diameter; thus, the narrowed portion of the flow channel of the FTEP device used to transform such bacterial cells will be at least 2 μm wide. In another example, if a mammalian cell is approximately 50 μm in diameter, the narrowed portion of the flow channel of the FTEP device used to transform such mammalian cells will be at least 100 μm wide. That is, the narrowed portion of the FTEP device will not physically contort or "squeeze" or occlude the cells being transformed.

In embodiments of the FTEP device where reservoirs are used to introduce cells and exogenous material into the FTEP device, the reservoirs range in volume from 100 µL to 10 mL, or from 500 µL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 µm are preferred. In another embodiment of the invention, the flow-through electroporation device comprises at least one additional electrode which applies a ground potential to the FTEP device.

Cell Singulation and Enrichment Device

Figure 6A:
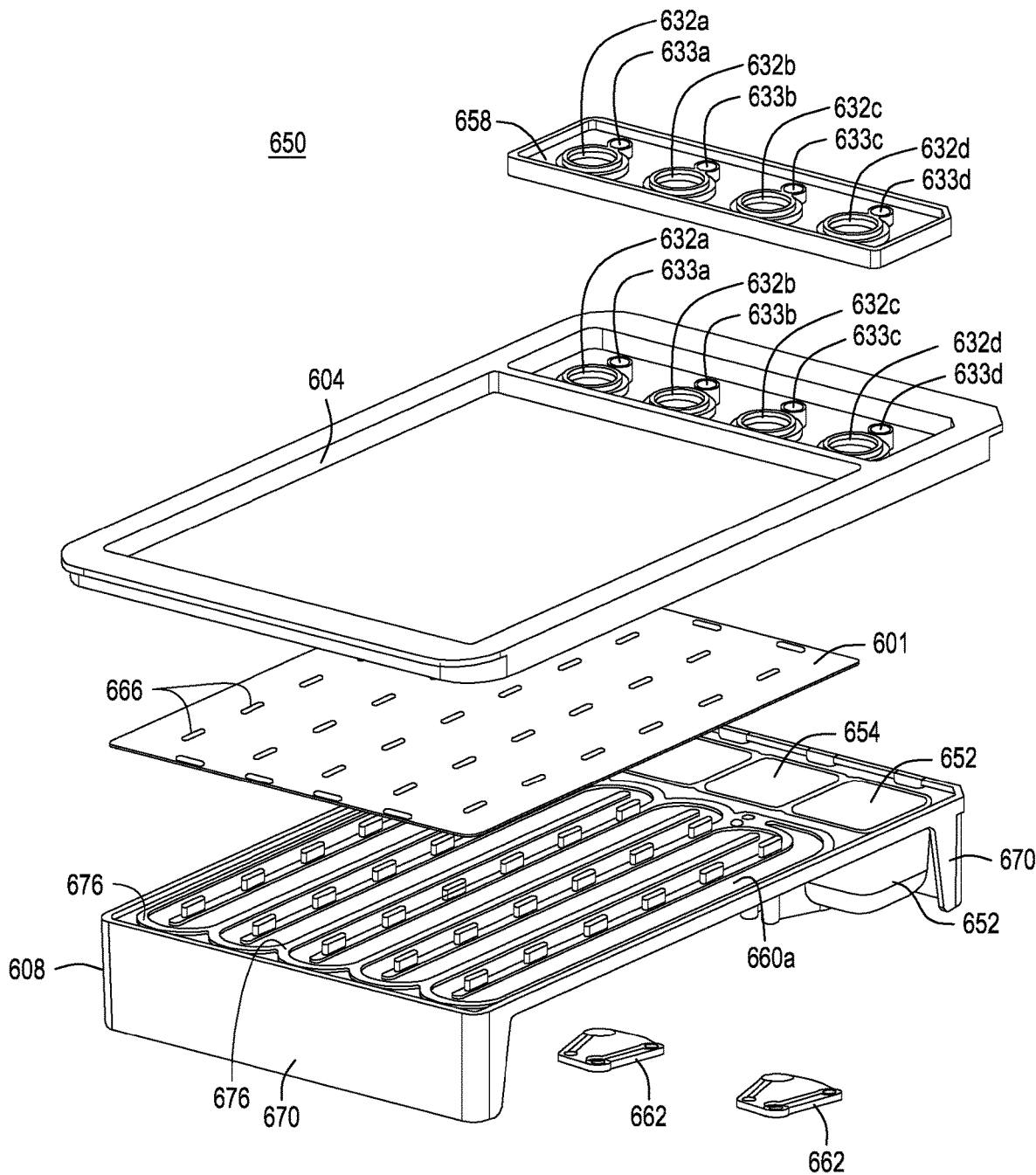
FIGS. 6A-6C depict an embodiment of a solid wall isolation incubation and normalization (SWIIN) module.

A module useful for performing the bacterial recovery, selection and editing methods depicted in FIG. 1A is a solid wall isolation, incubation, and normalization (SWIIN) module. FIG. 6A depicts an embodiment of a SWIIN module 650 from an exploded top perspective view. In SWIIN module 650 the retentate member is formed on the bottom of a top of a SWIIN module component and the permeate member is formed on the top of the bottom of a SWIIN module component.

The SWIIN module 650 in FIG. 6A comprises from the top down, a reservoir gasket or cover 658, a retentate member 604 (where a retentate flow channel cannot be seen in this FIG. 6A), a perforated member 601 swaged with a filter (filter not seen in FIG. 6A), a permeate member 608 comprising integrated reservoirs (permeate reservoirs 652 and retentate reservoirs 654), and two reservoir seals 662, which seal the bottom of permeate reservoirs 652 and retentate reservoirs 654. A permeate channel 660*a* can be seen disposed on the top of permeate member 608, defined by a raised portion 676 of serpentine channel 660*a*, and ultrasonic tabs 664 can be seen disposed on the top of permeate member 608 as well. The perforations that form the wells on perforated member 601 are not seen in this FIG. 6A; however, through-holes 666 to accommodate the ultrasonic tabs 664 are seen. In addition, supports 670 are disposed at either end of SWIIN module 650 to support SWIIN module 650 and to elevate permeate member 608 and retentate member 604 above reservoirs 652 and 654 to minimize bubbles or air entering the fluid path from the permeate reservoir to serpentine channel 660*a* or the fluid path from the retentate reservoir to serpentine channel 660*b* (neither fluid path is seen in this FIG. 6A).

In this FIG. 6A, it can be seen that the serpentine channel 660*a* that is disposed on the top of permeate member 608 traverses permeate member 608 for most of the length of permeate member 608 except for the portion of permeate member 608 that comprises permeate reservoirs 652 and retentate reservoirs 654 and for most of the width of permeate member 608. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 µm-200 µm in diameter, and the perforated member is approximately 125 µm deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 660*a* and 660*b* can have approximately the same volume or a different volume. For example, each "side" or portion 660*a*, 660*b* of the serpentine channel may have a volume of, e.g., 2 mL, or serpentine channel 660*a* of permeate member 608 may have a volume of 2 mL, and the serpentine channel 660*b* of retentate member 604 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 660*a* and 660*b* of the permeate member 608 and retentate member 604, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 6E and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, CA)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, MA) (also see Levin-Reisman, et al., Nature Methods, 7:737-39 (2010)). Cell growth for, e.g., mammalian cells may be monitored by, e.g., the growth monitor sold by IncuCyte (Ann Arbor, MI) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, NJ); Molecular Devices (QPix 400™ system, San Jose, CA); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 650 may be controlled by, e.g., moving heated air over the top of (e.g., retentate member) of the SWIIN module 650, or by applying a transparent heated lid over at least the serpentine channel portion 660*b* of the retentate member 604. See, e.g., FIG. 6F and the description thereof infra.

In SWIIN module 650 cells and medium—at a dilution appropriate for Poisson or substantial Poisson distribution of the cells in the microwells of the perforated member—are flowed into serpentine channel 660*b* from ports in retentate member 604, and the cells settle in the microwells while the medium passes through the filter into serpentine channel 660*a* in permeate member 608. The cells are retained in the microwells of perforated member 601 as the cells cannot travel through filter 603. Appropriate medium may be introduced into permeate member 608 through permeate ports 611. The medium flows upward through filter 603 to nourish the cells in the microwells (perforations) of perforated member 601. Additionally, buffer exchange can be effected by cycling medium through the retentate and permeate members. In operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 650 until the growth of the cell colonies in the microwells is normalized. For the normalization protocol, once the colonies are normalized, the colonies are flushed from the microwells by applying fluid or air pressure (or both) to the permeate member serpentine channel 660*a* and thus to filter 603 and pooled. Alternatively, if cherry picking is desired, the growth of the cell colonies in the microwells is monitored, and slow-growing colonies are directly selected; or, fast-growing colonies are eliminated.

Figure 6B:
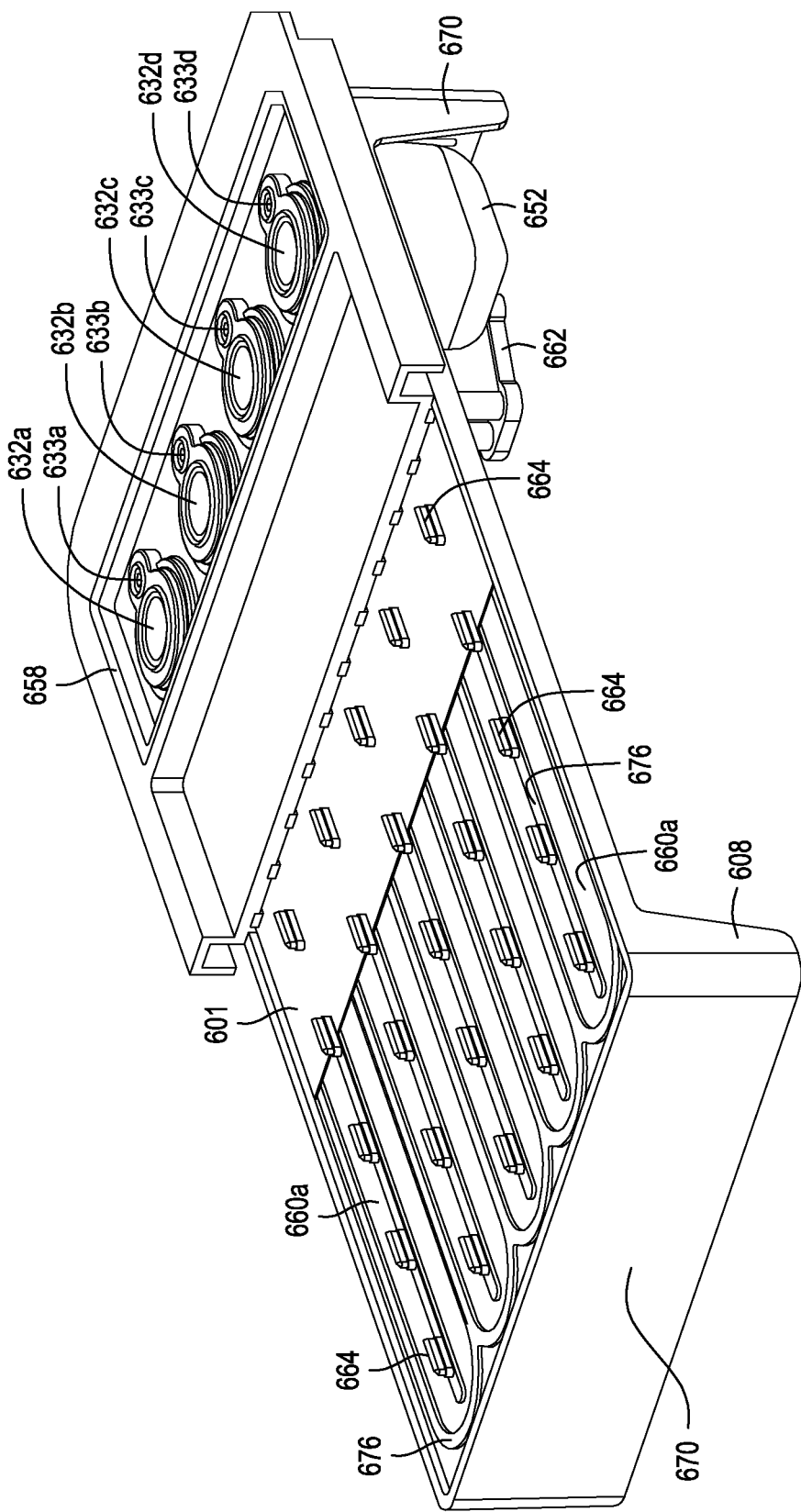

FIG. 6B is a top perspective view of a SWIIN module with the retentate and perforated members in partial cross section. In this FIG. 6C, it can be seen that serpentine channel 660*a* is disposed on the top of permeate member 608 is defined by raised portions 676 and traverses permeate member 608 for most of the length and width of permeate member 608 except for the portion of permeate member 608 that comprises the permeate and retentate reservoirs (note only one retentate reservoir 652 can be seen). Moving from left to right, reservoir gasket 658 is disposed upon the integrated reservoir cover 678 (cover not seen in this FIG. 6C) of retentate member 604. Gasket 658 comprises reservoir access apertures 632*a*, 632*b*, 632*c*, and 632*d*, as well as pneumatic ports 633*a*, 633*b*, 633*c* and 633*d*. Also at the far left end is support 670. Disposed under permeate reservoir 652 can be seen one of two reservoir seals 662. In addition to the retentate member being in cross section, the perforated member 601 and filter 603 (filter 603 is not seen in this FIG. 6C) are in cross section. Note that there are a number of ultrasonic tabs 664 disposed at the right end of SWIIN module 650 and on raised portion 676 which defines the channel turns of serpentine channel 660*a*, including ultrasonic tabs 664 extending through through-holes 666 of perforated member 601. There is also a support 670 at the end distal reservoirs 652, 654 of permeate member 608.

Figure 6C:
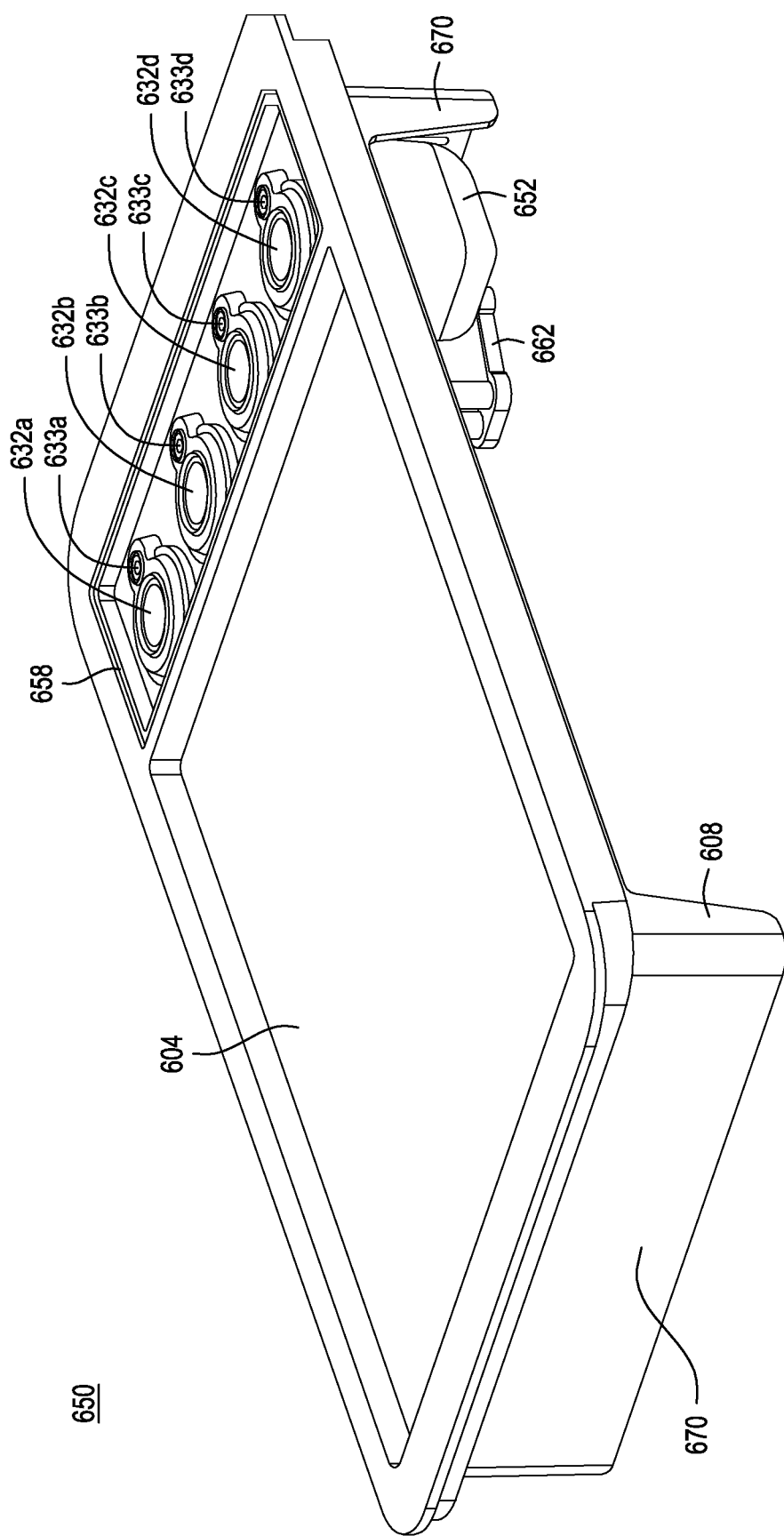

FIG. 6C is a side perspective view of an assembled SWIIN module 650, including, from right to left, reservoir gasket 658 disposed upon integrated reservoir cover 678 (not seen) of retentate member 604. Gasket 658 may be fabricated from rubber, silicone, nitrile rubber, polytetrafluoroethylene, a plastic polymer such as polychlorotrifluoroethylene, or other flexible, compressible material. Gasket 658 comprises reservoir access apertures 632*a*, 632*b*, 632*c*, and 632*d*, as well as pneumatic ports 633*a*, 633*b*, 633*c* and 633*d*. Also at the far-left end is support 670 of permeate member 608. In addition, permeate reservoir 652 can be seen, as well as one reservoir seal 662. At the far-right end is a second support 670.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 660.

Figure 6D:
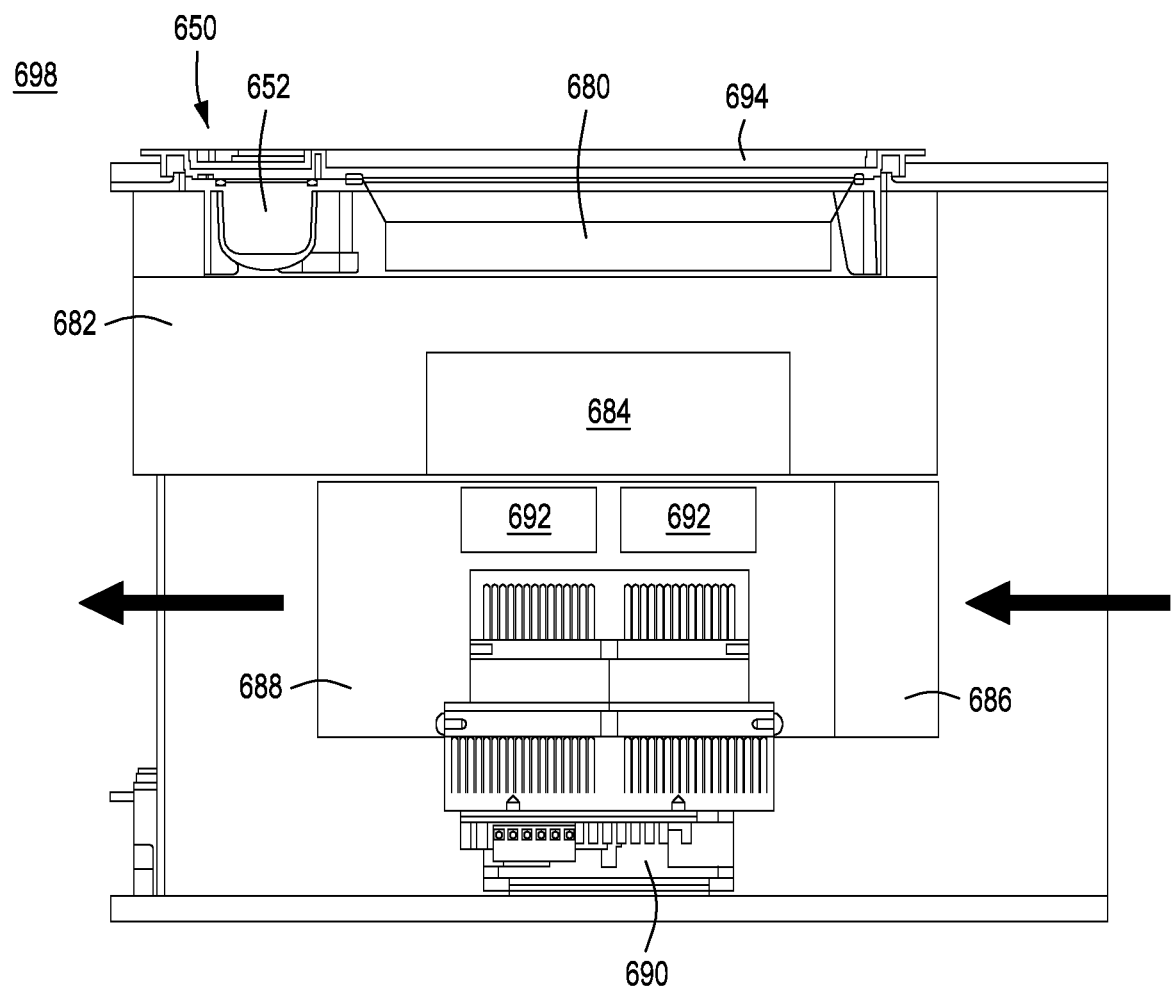
FIG. 6D depicts the embodiment of the SWIIN module in FIGS. 6A-6C further comprising a heater and a heated cover.

FIG. 6D depicts the embodiment of the SWIIN module in FIGS. 6A-6C further comprising a heat management system including a heater and a heated cover. The heater cover facilitates the condensation management that is required for imaging. Assembly 698 comprises a SWIIN module 650 seen lengthwise in cross section, where one permeate reservoir 652 is seen. Disposed immediately upon SWIIN module 650 is cover 694 and disposed immediately below SWIIN module 650 is backlight 680, which allows for imaging. Beneath and adjacent to the backlight and SWIIN module is insulation 682, which is disposed over a heatsink 684. In this FIG. 6E, the fins of the heatsink would be in-out of the page. In addition there is also axial fan 686 and heat sink 688, as well as two thermoelectric coolers 692, and a controller 690 to control the pneumatics, thermoelectric coolers, fan, solenoid valves, etc. The arrows denote cool air coming into the unit and hot air being removed from the unit. It should be noted that control of heating allows for growth of many different types of cells (prokaryotic and eukaryotic) as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Ser. No. 16/399,988, filed 30 Apr. 2019; Ser. No. 16/454,865, filed 26 Jun. 2019; and Ser. No. 16/540,606, filed 14 Aug. 2019. For alternative isolation, incubation and normalization modules, see U.S. Ser. No. 16/536,049, filed 8 Aug. 2019.

It should be apparent to one of ordinary skill in the art given the present disclosure that the process described may be recursive and multiplexed; that is, cells may go through an editing workflow, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells.

Curing can be accomplished by, e.g., cleaving the vector(s) using a curing plasmid thereby rendering the editing and/or engine vector (or single, combined engine/editing vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine vector.

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Editing Cassette and Backbone Amplification and Assembly

Editing Cassette Preparation: 5 nM oligonucleotides synthesized on a chip were amplified using Q5 polymerase in 50 µL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 300 µL SPRI mix was added to the 50 µL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 μL 0.5×TE pH 8.0 was added to the tubes, and the beads were vortexed to mix. The slurry was incubated at room temperature for 2 minutes, then subjected to the magnetic field for 2 minutes. The eluate was removed and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation: A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 μL ddH$_2$O and quantified before nucleic acid assembly.

Isothermal Nucleic Acid Assembly: 150 ng backbone DNA was combined with 100 ng cassette DNA. An equal volume of 2× Gibson Master Mix was added, and the reaction was incubated for 45 minutes at 50° C. After assembly, the assembled backbone and cassettes were subjected to SPRI cleanup, as described above.

Example II: Preparation of Competent Cells

A 1 mL aliquot of a freshly-grown overnight culture of MG1655 strain *E. coli* cells transformed with the engine vector was added to a 250 mL flask containing 100 mL LB/SOB+25 m/mL chlor medium. The cells were grown to 0.4-0.7 OD, and cell growth was halted by transferring the culture to ice for 10 minutes. The cells were pelleted at 8000×g in a JA-18 rotor for 5 minutes, washed 3× with 50 mL ice cold ddH$_2$O or 10% glycerol, and pelleted at 8000×g in JA-18 rotor for 5 minutes. The washed cells were resuspended in 5 mL ice cold 10% glycerol and aliquoted into 200 μL portions. Optionally at this point the glycerol stocks could be stored at −80° C. for later use.

Example III: Creation of New Cell Lines Transformed with Engine Vectors

Transformation: 1 μL of each of the different engine vector DNA (e.g., one of the p19'7, p-197-recA or p197-srpRrecA engine vector) was added to 50 μL MG1655 strain *E. coli* cells. The transformed cells were plated on LB plates with 25 m/mL chloramphenicol (chlor) and incubated overnight to accumulate clonal isolates. The next day, a colony was picked, grown overnight in LB+25 m/mL chlor, and glycerol stocks were prepared from the saturated overnight culture by adding 500 μL 50% glycerol to 1000 μL culture. The stocks of *E. coli* cells comprising the different engine vectors were frozen at −80° C.

Example IV: Transformation of Editing Vector (Triple Edit) into E Cloni®

Transformation: 20 μL of the prepared editing vector Gibson Assembly reaction was added to 30 μL chilled water along with 10 μL E cloni® (Lucigen, Middleton, WI) supreme competent cells. An aliquot of the transformed cells were spot plated to check the transformation efficiency, where >100× coverage was required to continue. The transformed E cloni® cells were outgrown in 25 mL SOB+100 m/mL carbenicillin (carb). Glycerol stocks were generated from the saturated culture by adding 500 μL 50% glycerol to 1000 μL saturated overnight culture. The stocks were frozen at −80° C. This step is optional, providing a ready stock of the cloned editing library. Alternatively, Gibson or another assembly of the editing cassettes and the vector backbone can be performed before each editing experiment. In this experiment, a 60-member triple editing plasmid pool was used, where each editing plasmid targeted three genes: xylA, lacZ and galK.

Example V: Standard Plating Protocol

This protocol describes a standard plating protocol for nucleic acid-guided nuclease editing of bacterial cells. Materials: Outside of standard molecular biology tools, the following will be necessary:

TABLE 1

| Product | Vendor |
| --- | --- |
| SOB | Teknova |
| LB | Teknova |
| LB agar plate with chloramphenicol/carbenicillin and 1% arabinose | Teknova |

Protocol: Immediately after transformation with the editing plasmid library, the cell/DNA mixture was transferred to a culture tube containing 2.7 mL of SOB medium. Preparing 2.7 mL aliquots in 14 mL culture tubes prior to electroporation allowed for a faster recovery of cells; the final volume of the recovery was 3 mL. All culture tubes were placed into a shaking incubator set to 250 RPM and 30° C. for three hours. While the cultures were recovering, the necessary number of LB agar plates with chloramphenicol and carbenicillin+1% arabinose were removed from the refrigerator and warmed to room temperature. Multiple dilutions were used for each plating so as to have countable and isolated colonies on the plates. Plating suggestions:

TABLE 2

| Sequencing type | Dilution(s) suggested | Volume to plate |
| --- | --- | --- |
| SinglePlex | $10^{-1}$ through $10^{-3}$ | 300 uL |
| Amplicon | None | 300 uL (= 1/10$^{th}$ recovery) |

After three hours, the culture tubes were removed from the shaking incubator. First, plating for amplicon sequencing was performed by following the above table. Plating beads were used to evenly distribute the culture over the agar. The beads were removed from the plate the plate was allowed to dry uncovered in a flow hood. While the plates were drying, the remaining culture was used to perform serial dilutions, where the standard dilutions were 50 μL of culture into 450 uL of sterile, 0.8% NaCl. The plate/tubes used for these dilutions (as well as the original culture) were maintained at 4° C. in case additional dilutions were needed to be performed based on colony counts. Plating for whole genome sequencing was performed according to the Table 2. Additional or fewer dilutions may be used based on library/ competent cell knowledge. The cultures were evenly spread across the agar using sterile, plating beads. The beads were then removed from the plate and the plates were allowed to dry uncovered in the flow hood. The plates were incubated at 30° C. for 18 hours then the agar plates were removed from the incubator. If editing has been successful there will be a phenotypic readout on MacConkey agar.

Figure 7A:
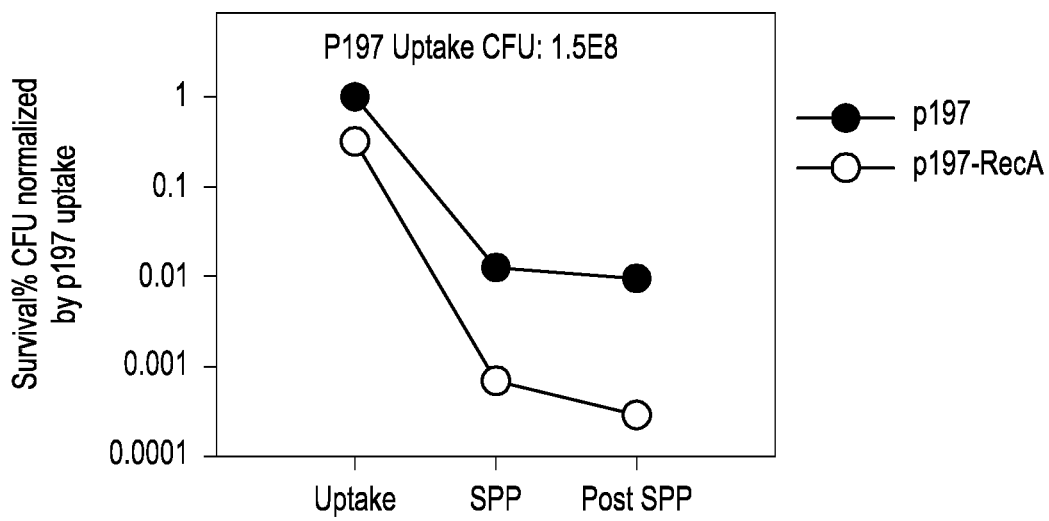
FIG. 7A shows the CFUs obtained for E. coli transformed with the p197 engine vector vs. the p197-recA engine vector at uptake, at plating, and post-plating.
Figure 7B:
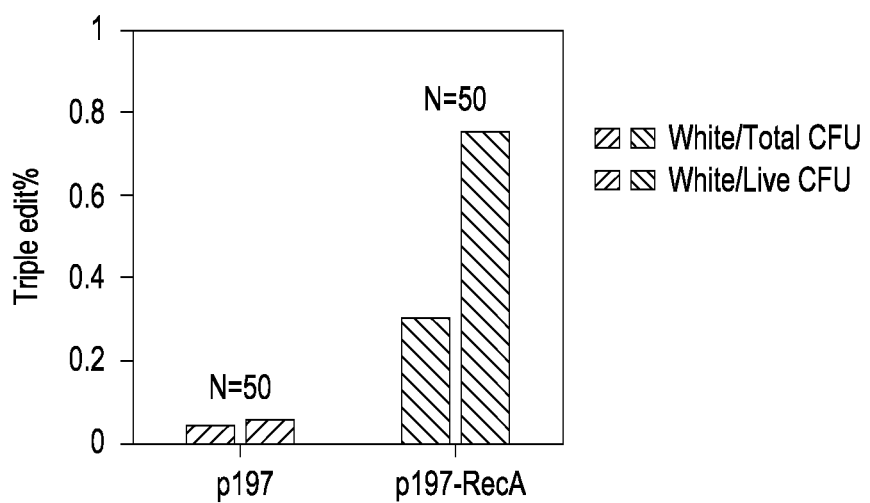
FIG. 7B shows the percentage of triple simultaneous edits for E. coli cells transformed with the p197 engine vector vs. the p197-recA engine vector.

The results for the p197 and p197-recA engine plasmids are shown in FIGS. 7A and 7B. Note in FIG. 7A the p197-recA engine plasmid reduced post-plating CFUs by almost 2-orders of magnitude; however, 15/20 colonies that grew were triple editors (see FIG. 7B). That is, if the cells did survive, 75% were triple editors.

The results for survival and percent editing for the p19'7, p197-recA, and p19'7-srpRrecA engine plasmids are shown in FIG. 8A-8C. FIG. 8A shows the CFUs obtained for *E. coli* transformed with the p197 engine vector, the p197-recA engine vector, and the p197-srpRrecA engine vector at uptake, at plating, and post-plating. Note that the post-plating CFU for the p197-srpRrecA engine plasmid was comparable to that obtained with p197; however, the p197-recA engine plasmid had a low post-plating CFU. FIG. 8B shows the editing CFU and percentage of triple simultaneous edits for *E. coli* cells transformed with the p197 engine vector, the p197-recA engine vector and the p197-srpRrecA engine vector. Note that although the overall editing rate for the p197-srpRrecA engine vector was lower than the p-197-recA engine vector, the rate for edited CFU is higher. FIG. 8C is a table reporting the post-plating survival rate and the percentage editing rate for *E. coli* cells reported in the graph in FIG. 8B. Note that the edit percentage for the p197 engine vector is approximately 5%, the edit percentage for the p197-recA engine vector is approximately 75%, and the edit percentage for the p197-srpRrecA engine vector is approximately 42%.

Example IV: Fully-Automated Singleplex RGN-Directed Editing Run

Singleplex automated genomic editing using MAD7 nuclease was successfully performed with an automated multi-module instrument of the disclosure. For examples of multi-module cell editing instruments, see U.S. Pat. No. 10,253,316, issued 9 Apr. 2019; U.S. Pat. No. 10,329,559, issued 25 Jun. 2019; and U.S. Pat. No. 10,323,242, issued 18 Jun. 2019; and U.S. Ser. No. 16/412,175, filed 14 May 2019; Ser. No. 16/412,195, filed 14 May 2019; and Ser. No. 16/423,289, filed 28 May 2019, all of which are herein incorporated by reference in their entirety.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example V: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in an isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product nonfunctional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent *E. Coli* cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method for increasing observed editing in a multiplexed CRISPR nuclease editing system in bacteria comprising:
   (a) providing bacteria cells, wherein each of the bacteria cells comprises
      (i) an engine vector comprising:
         (A) a first inducible promoter driving expression of a coding sequence for a CRISPR nuclease;
         (B) a bacterial origin of replication; and
         (C) a first selection marker; and
      (ii) an editing vector comprising a second inducible promoter or a constitutive promoter driving expression of a coding sequence for a recA protein, wherein the second inducible promoter or the constitutive promoter drives transcription of at least two editing cassettes, wherein each editing cassette comprises:
         (A) a gRNA sequence and a donor DNA sequence to be transcribed;
         (B) a bacterial origin or replication; and
         (C) a second selection marker;
   (b) allowing transcription of the recA protein and the at least two editing cassettes from the second inducible promoter or the constitutive promoter; and
   (c) following transcription of the recA protein and the at least two editing cassettes, inducing transcription of the CRISPR nuclease to produce edited cells.

2. The method of claim 1, wherein the CRISPR nuclease is MAD7.

3. The method of claim 1, wherein the CRISPR nuclease is Cas9.

4. The method of claim 1, wherein the coding sequence for the recA protein is a coding sequence for a recA fusion protein.

5. The method of claim 4, wherein the recA fusion protein is a recA-srpR fusion protein.

6. The method of claim 5, wherein the recA-srpR fusion protein comprises an in-frame fusion protein comprising a coding sequence of the srpR protein at an N-terminal portion of the in-frame fusion protein and the coding sequence for the recA protein coding sequence at a C-terminal portion of the in-frame fusion protein.

7. The method of claim 1, wherein the engine vector comprises a coding sequence for cI857 and the inducible promoter is a pL promoter driving expression of the CRISPR nuclease.

8. The method of claim 1, wherein the engine vector further comprises coding sequences for a λRed recombineering system.

9. The method of claim 1, wherein the second inducible promoter is a pL inducible promoter.

10. The method of claim 1, wherein the first and second selection markers are different selection markers.

11. The method of claim 1, wherein the method further comprises:
   (d) providing to the edited cells:
      a second editing vector comprising the second inducible promoter or the constitutive promoter driving expression of a coding sequence for a recA protein, wherein the second inducible promoter or the constitutive promoter drives transcription of at least two editing cassettes, wherein each editing cassette comprises:
         (A) a gRNA sequence and a donor DNA sequence to be transcribed;
         (B) a bacterial origin or replication; and
         (C) a third selection marker;
   (e) allowing transcription of the recA protein and the at least two editing cassettes from the second inducible promoter or the constitutive promoter; and
   (f) following transcription of the recA protein and the at least two editing cassettes, inducing transcription of the CRISPR nuclease to produce twice edited cells.

12. A method for increasing observed editing in a multiplexed CRISPR nuclease editing system in bacteria comprising:
   (A) providing bacteria cells, wherein each of the bacteria cells comprises:
      (i) an engine vector comprising:
         (a) a first inducible promoter driving expression of a coding sequence for a CRISPR nuclease;
         (b) a bacterial origin of replication;
         (c) a λRed recombineering system; and
         (d) a first selection marker;
      (ii) an editing vector comprising:
         (a) a second inducible promoter or a constitutive promoter driving expression of a coding sequence for a recA protein;

(b) the second inducible promoter or the constitutive promoter driving transcription of at least two editing cassettes wherein each editing cassette comprises a gRNA sequence and a donor DNA sequence to be transcribed;
(c) a bacterial origin or replication; and
(d) a second selection marker;
(B) allowing transcription of the recA protein and the at least two editing cassettes from the second inducible promoter or the constitutive promoter; and
(C) following transcription of the recA protein and the at least two editing cassettes, inducing transcription of the CRISPR nuclease to produce edited cells.

13. The method of claim 12, wherein the CRISPR nuclease is MAD7.

14. The method of claim 12, wherein the CRISPR nuclease is Cas9.

15. The method of claim 12, wherein the coding sequence for the recA protein is a coding sequence for a recA fusion protein.

16. The method of claim 15, wherein the recA fusion protein is a recA-srpR fusion protein.

17. The method of claim 16, wherein the recA-srpR fusion protein comprises an in-frame fusion protein comprising a coding sequence of the srpR protein at an N-terminal portion of the in-frame fusion protein and the coding sequence for the recA protein coding sequence at a C-terminal portion of the in-frame fusion protein.

18. The method of claim 12, wherein the engine vector comprises a coding sequence for c1857 and an inducible pL promoter drives expression of the CRISPR nuclease and the at least two editing cassettes.

19. The method of claim 12, wherein the first and second selection markers are different selection markers.

20. The method of claim 12, wherein the method further comprises: (D) growing the edited cells in colonies until the cell colonies become normalized to produce normalized cells; and (E) pooling the normalized cells.

* * * * *